(12) United States Patent
Himmelsbach et al.

(10) Patent No.: US 7,220,750 B2
(45) Date of Patent: *May 22, 2007

(54) BICYCLIC HETEROCYCLES, PHARMACEUTICAL COMPOSITIONS CONTAINING THESE COMPOUNDS, THEIR USE AND PROCESSES FOR PREPARING THEM

(75) Inventors: Frank Himmelsbach, Mittelbiberach (DE); Elke Langkopf, Warthausen (DE); Thomas Metz, Vienna (AT); Flavio Solca, Vienna (AT); Birgit Jung, Schwabenheim (DE); Anke Baum, Vienna (AT)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 296 days.

This patent is subject to a terminal disclaimer.

(21) Appl. No.: 10/016,280

(22) Filed: Dec. 10, 2001

(65) Prior Publication Data

US 2002/0169180 A1 Nov. 14, 2002

Related U.S. Application Data

(63) Continuation of application No. PCT/EP00/05547, filed on Jun. 16, 2000.

(60) Provisional application No. 60/146,644, filed on Jul. 30, 1999.

(30) Foreign Application Priority Data

Jun. 21, 1999 (DE) ............... 199 28 281
May 11, 2000 (DE) ............... 100 23 085

(51) Int. Cl.
*A61K 31/517* (2006.01)
*A61K 31/47* (2006.01)
*C07D 239/72* (2006.01)
*C07D 215/38* (2006.01)

(52) U.S. Cl. ............... 514/266.4; 514/256; 514/266.1; 544/242; 544/253; 544/283; 544/293

(58) Field of Classification Search ............... 514/183, 514/266.1, 266.4, 256, 313; 544/253, 283, 544/293, 242
See application file for complete search history.

(56) References Cited

U.S. PATENT DOCUMENTS 6,627,634 B2 * 9/2003 Himmelsbach et al. 514/266.22

2002/0173509 A1 * 11/2002 Himmelsbach et al. .. 514/234.5
2004/0158065 A1 * 8/2004 Barth et al. ................. 544/284

FOREIGN PATENT DOCUMENTS

| EP | 566226 | * 10/1993 |
|---|---|---|
| WO | WO 95/20045 | 7/1995 |
| WO | WO 96/30347 | 10/1996 |
| WO | WO 96/33980 | 10/1996 |
| WO | WO 97/02266 | 1/1997 |
| WO | 9738983 | * 10/1997 |
| WO | WO 9738983 A1 | 10/1997 |
| WO | WO 98/43960 | 10/1998 |
| WO | WO 9843960 A1 | 10/1998 |
| WO | 9909016 | * 2/1999 |
| WO | WO 9906378 A1 | 2/1999 |
| WO | WO 99/35146 | 7/1999 |
| WO | WO 00/31068 | 6/2000 |
| WO | 00/78735 A1 | * 12/2000 |

OTHER PUBLICATIONS

Chemical Abstract DN 120:217715, also cited as EP566226.*
Chemical Abstract DN 130:196664, also cited as WO9909016.*

* cited by examiner

*Primary Examiner*—James O. Wilson
*Assistant Examiner*—Tamthom N. Truong
(74) *Attorney, Agent, or Firm*—Michael P. Morris; Mary-Ellen Devlin; Paula K. Wittmayer

(57) ABSTRACT

The present invention relates to bicyclic heterocycles of general formula

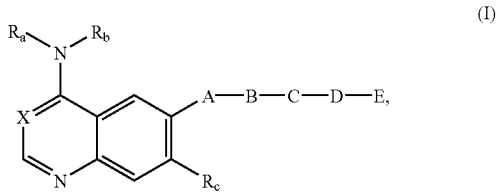

wherein $R_a$ to $R_c$, A to E and X are defined as in claim 1, the tautomers, stereoisomers and salts thereof, particularly the physiologically acceptable salts thereof with inorganic or organic acids or bases which have valuable pharmacological properties, in particular an inhibitory effect on signal transduction mediated by tyrosine kinases, their use in the treatment of diseases, especially tumoral diseases and diseases of the lungs and airways, and the preparation thereof.

9 Claims, No Drawings

BICYCLIC HETEROCYCLES, PHARMACEUTICAL COMPOSITIONS CONTAINING THESE COMPOUNDS, THEIR USE AND PROCESSES FOR PREPARING THEM

This is a continuation of PCT/EP 00/05547 filed on Jun. 16, 2000, which claims benefit to prior U.S. Provisional Application 60/146,644, filed Jul. 30, 1999 and prior German Application Nos. DE 199 28 281 and DE 100 23 085, filed Jun. 21, 1999 and May 11, 2000, respectively. Benefit of the earlier filing date of the prior International Application is hereby claimed pursuant to 35 U.S.C. § 365(c).

The present invention relates to bicyclic heterocycles of general formula

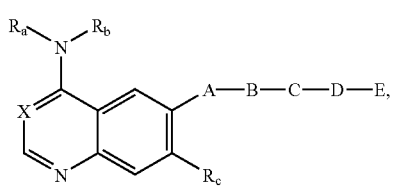

the tautomers, the stereoisomers and the salts thereof, particularly the physiologically acceptable salts thereof with inorganic or organic acids or bases which have valuable pharmacological properties, particularly an inhibitory effect on signal transduction mediated by tyrosine kinases, the use thereof for treating diseases, particularly tumoral diseases, diseases of the lungs and respiratory tract, and the preparation thereof.

In the above general formula I:

$R_a$ denotes a hydrogen atom or a $C_{1-4}$-alkyl group, $R_b$ denotes a phenyl, benzyl or 1-phenylethyl group wherein the phenyl nucleus is substituted in each case by the groups $R_1$ to $R_3$, whilst $R_1$ and $R_2$, which may be identical or different, in each case denote a hydrogen, fluorine, chlorine, bromine or iodine atom, a $C_{1-4}$-alkyl, hydroxy, $C_{1-4}$-alkoxy, $C_{3-6}$-cycloalkyl, $C_{4-6}$-cycloalkoxy, $C_{2-5}$-alkenyl or $C_{2-5}$-alkynyl group, an aryl, aryloxy, arylmethyl or arylmethoxy group, a $C_{3-5}$-alkenyloxy or $C_{3-5}$-alkynyloxy group, whilst the unsaturated moiety may not be linked to the oxygen atom, a $C_{1-4}$-alkylsulfenyl, $C_{1-4}$-alkylsulfinyl, $C_{1-4}$-alkylsulfonyl, $C_{1-4}$-alkylsulfonyloxy, trifluoromethylsulfenyl, trifluoromethylsulfinyl or trifluoromethylsulfonyl group, a methyl or methoxy group substituted by 1 to 3 fluorine atoms, an ethyl or ethoxy group substituted by 1 to 5 fluorine atoms, a cyano or nitro group or an amino group optionally substituted by one or two $C_{1-4}$-alkyl groups, wherein the substituents may be identical or different, or $R_1$ together with $R_2$, if they are bound to adjacent carbon atoms, denote a —CH=CH—CH=CH, —CH=CH—NH or —CH=N—NH group and $R_3$ denotes a hydrogen, fluorine, chlorine or bromine atom, a $C_{1-4}$-alkyl, trifluoromethyl or $C_{1-4}$-alkoxy group, X denotes a methine group substituted by a cyano group or a nitrogen atom, A denotes an imino group optionally substituted by a $C_{1-4}$-alkyl group, B denotes a carbonyl or sulfonyl group, C denotes a 1,3-allenylene, 1,1- or 1,2-vinylene group which may be substituted in each case by one or two methyl groups or by a trifluoromethyl group, an ethynylene group or a 1,3-butadien-1,4-ylene group optionally substituted by 1 to 4 methyl groups or by a trifluoromethyl group, D denotes an alkylene, —CO-alkylene or —SO$_2$-alkylene group wherein the alkylene moiety in each case contains 1 to 8 carbon atoms and additionally 1 to 4 hydrogen atoms in the alkylene moiety may be replaced by fluorine atoms, whilst the linking of the —CO-alkylene or —SO$_2$-alkylene group to the adjacent group C in each case must take place via the carbonyl or sulfonyl group, a —CO—O-alkylene, —CO—NR$_4$-alkylene or —SO$_2$—NR$_4$-alkylene group wherein the alkylene moiety in each case contains 1 to 8 carbon atoms, whilst the linking to the adjacent group C in each case must take place via the carbonyl or sulfonyl group, wherein $R_4$ denotes a hydrogen atom or a $C_{1-4}$-alkyl group, or, if D is bound to a carbon atom of the group E, it may also denote a bond or, if D is bound to a nitrogen atom of the group E, it may also denote a carbonyl or sulfonyl group, E denotes an amino, $C_{1-4}$-alkylamino or di-($C_{1-4}$-alkyl)-amino group wherein the alkyl moieties may be identical or different, a $C_{2-4}$-alkylamino group wherein the alkyl moiety is substituted in β-, γ-, or δ-position with regard to the nitrogen atom of the amino group by the group $R_5$, whilst $R_5$ denotes a hydroxy, $C_{1-4}$-alkoxy, amino, $C_{1-4}$-alkylamino or di-($C_{1-4}$-alkyl)-amino group, a 4- to 7-membered alkyleneimino group optionally substituted by one or two methyl groups or a 6- to 7-membered alkyleneimino group optionally substituted by one or two methyl groups wherein in each case a methylene group in position 4 is replaced by an oxygen or sulfur atom, by a sulfinyl, sulfonyl, imino or N-($C_{1-95\ 4}$-alkyl)-imino group, an N-($C_{1-4}$-alkyl)-N-($C_{2-4}$-alkyl)-amino group wherein the $C_{2-4}$-alkyl moiety is substituted in β-, γ-, or δ-position with regard to the nitrogen atom of the amino group by the group $R_5$, whilst $R_5$ is as hereinbefore defined, a di-($C_{2-4}$-alkyl)-amino group wherein the two $C_{2-4}$-alkyl moieties are substituted in each case in β-, γ-, or δ-position with regard to the nitrogen atom of the amino group by the group $R_5$, whilst the substituents may be identical or different and $R_5$ is as hereinbefore defined, a $C_{3-7}$-cycloalkylamino or $C_{3-7}$-cycloalkyl-$C_{1-3}$-alkylamino group wherein in each case the nitrogen atom may be substituted by a further $C_{1-4}$-alkyl group, an amino or $C_{1-4}$-alkylamino group wherein in each case the nitrogen atom is substituted by a tetrahydrofuran-3-yl, tetrahydropyran-3-yl, tetrahydropyran-4-yl, tetrahydrofuranylmethyl, 1-(tetrahydrofuran-3-yl)piperidin-4-yl, 1-(tetrahydropyran-3-yl)piperidin-4-yl, 1-(tetrahydropyran-4-yl)piperidin-4-yl, 3-pyrrolidinyl, 3-piperidinyl, 4-piperidinyl, 3-hexahydro-azepinyl or 4-hexahydro-azepinyl group optionally substituted by 1 to 3 $C_{1-4}$-alkyl groups, a 4- to 7-membered alkyleneimino group optionally substituted by 1 to 4 $C_{1-2}$-alkyl groups, which may be substituted by the group $R_5$ either at a cyclic carbon atom or at one of the alkyl groups, whilst $R_5$ is as hereinbefore defined, a piperidino group substituted by a tetrahydrofuranyl, tetrahydropyranyl or tetrahydrofuranylmethyl group, a 6- to 7-membered alkyleneimino group optionally substituted by 1 or 2 $C_{1-2}$-alkyl groups wherein a methylene group in each case is replaced in the 4 position by an oxygen or sulfur atom, by an imino group substituted by the group $R_6$, or by a sulfinyl or sulfonyl group, whilst $R_6$ denotes a hydrogen atom, a $C_{1-4}$-alkyl, 2-methoxyethyl, 3-methoxypropyl, $C_{3-7}$-cycloalkyl, $C_{3-7}$-cycloalkyl-$C_{1-4}$-alkyl, tetrahydrofuran-3-yl, tetrahydropyran-3-yl, tetrahydropyran-4-yl, tetrahydrofuranylmethyl, formyl, $C_{1-4}$-alkylcarbonyl, $C_{1-4}$-alkylsulfonyl, aminocarbonyl, $C_{1-4}$-alkylaminocarbonyl or di-($C_{1-4}$-alkyl)-aminocarbonyl group, an imidazolyl group optionally substituted by 1 to 3 methyl groups, a $C_{5-7}$-cycloalkyl group wherein a methylene group is replaced by an oxygen or sulfur atom, by an imino group substituted by the group $R_6$, by a sulfinyl or sulfonyl group, whilst $R_6$ is as hereinbefore defined, or D together with E denotes a hydrogen, fluorine or chlorine atom, a $C_{1-4}$-alkyl group optionally substituted by 1 to 5 fluorine atoms, a $C_{3-6}$-cycloalkyl group, an aryl, heteroaryl, $C_{1-4}$-alkylcarbonyl or arylcarbonyl group, a carboxy, $C_{1-4}$-alkoxycarbonyl, aminocarbonyl, $C_{1-4}$-alkylaminocarbonyl or di-($C_{1-4}$-alkyl)-aminocarbonyl group or a carbonyl which is substituted by a 4- to 7-membered alkyleneimino group, whilst in the abovementioned 6- to 7-membered alkyleneimino groups in each case a methylene group may be replaced in the 4 position by an oxygen or sulfur atom, by an imino group substituted by the group $R_6$, by a sulfinyl or sulfonyl group, whilst $R_6$ is as hereinbefore defined, and $R_c$ denotes a $C_{4-7}$-cycloalkoxy or $C_{3-7}$-cycloalkyl-$C_{1-6}$-alkoxy group wherein the cycloalkyl moiety in each case may be substituted by a $C_{1-3}$-alkyl, hydroxy, $C_{1-4}$-alkoxy, amino, $C_{1-4}$-alkylamino, di-($C_{1-4}$-alkyl)-amino, pyrrolidino, piperidino, morpholino, piperazino, N-($C_{1-2}$-alkyl)-piperazino, hydroxy-$C_{1-2}$-alkyl, $C_{1-4}$-alkoxy-$C_{1-2}$-alkyl, amino-$C_{1-2}$-alkyl, $C_{1-4}$-alkylamino-$C_{1-2}$-alkyl, di-($C_{1-4}$-alkyl)-amino-$C_{1-2}$-alkyl, pyrrolidino-$C_{1-2}$-alkyl, piperidino-$C_{1-2}$-alkyl, morpholino-$C_{1-2}$-alkyl, piperazino-$C_{1-2}$-alkyl or N-($C_{1-2}$-alkyl)-piperazino-$C_{1-2}$-alkyl group, whilst the abovementioned monosubstituted cycloalkyl moieties may additionally be substituted by a $C_{1-3}$-alkyl group, a tetrahydrofuran-3-yloxy, tetrahydropyran-3-yloxy, tetrahydropyran-4-yloxy or tetrahydrofuranylmethoxy group, an $C_{2-4}$-alkoxy group substituted in β-, γ-, or δ-position with regard to the oxygen atom by an azetidin-1-yl, 4-methyl-homopiperazino or 4-ethyl-homopiperazino group, a 3-pyrrolidinyloxy, 2-pyrrolidinyl-$C_{1-4}$-alkyloxy, 3-pyrrolidinyl-$C_{1-4}$-alkyloxy, 3-piperidinyloxy, 4-piperidinyloxy, 2-piperidinyl-$C_{1-4}$-alkyloxy, 3-piperidinyl-$C_{1-4}$-alkyloxy, 4-piperidinyl-$C_{1-4}$-alkyloxy, 3-hexahydro-azepinyloxy, 4-hexahydro-azepinyloxy, 2-hexahydro-azepinyl-$C_{1-4}$-alkyloxy, 3-Hexahydro-azepinyl-$C_{1-4}$-alkyloxy or 4-hexahydro-azepinyl-$C_{1-4}$-alkyloxy group wherein in each case the cyclic nitrogen atom is substituted by the group $R_6$, where $R_6$ is as hereinbefore defined, particularly those compounds of general formula I wherein $R_a$, $R_b$, A to C and X are as hereinbefore defined, E denotes an amino, $C_{1-4}$-alkylamino or di-($C_{1-4}$-alkyl)-amino group wherein the alkyl moieties may be identical or different, a $C_{2-4}$-alkylamino group wherein the alkyl moiety is substituted from position 2 by the group $R_5$, whilst $R_5$ denotes a hydroxy, $C_{1-4}$-alkoxy, amino, $C_{1-4}$-alkylamino or di-($C_{1-4}$-alkyl)-amino group, a 4- to 7-membered alkyleneimino group optionally substituted by one or two methyl groups or a 6- to 7-membered alkyleneimino group optionally substituted by one or two methyl groups wherein in each case a methylene group in position 4 is replaced by an oxygen or sulfur atom, by a sulfinyl, sulfonyl, imino or N-($C_{1-4}$-alkyl)-imino group, an N-($C_{1-4}$-alkyl)-N-($C_{2-4}$-alkyl)-amino group wherein the $C_{2-4}$-alkyl moiety is substituted from position 2 onwards by the group $R_5$, where $R_5$ is as hereinbefore defined, a di-($C_{2-4}$-alkyl)-amino group wherein the two $C_{2-4}$-alkyl moieties are substituted in each case from position 2 onwards by the group $R_5$, whilst the substituents may be identical or different and $R_5$ is as hereinbefore defined, a $C_{3-7}$-cycloalkylamino or $C_{3-7}$-cycloalkyl-$C_{1-3}$-alkylamino group wherein in each case the nitrogen atom may be substituted by a further $C_{1-4}$-alkyl group, an amino or $C_{1-4}$-alkylamino group wherein in each case the nitrogen atom is substituted by a 3-pyrrolidinyl, 3-piperidinyl, 4-piperidinyl, 3-hexahydro-azepinyl or 4-hexahydro-azepinyl group optionally substituted by 1 to 3 $C_{1-4}$-alkyl groups, a 4- to 7-membered alkyleneimino group optionally substituted by 1 to 4 $C_{1-2}$-alkyl groups, which may be substituted by the group $R_5$ either at a cyclic carbon atom or at one of the alkyl groups, whilst $R_5$ is as hereinbefore defined, or a 6- to 7-membered alkyleneimino group optionally substituted by 1 or 2 $C_{1-2}$-alkyl groups wherein a methylene group in each case is replaced in the 4 position by an oxygen or sulfur atom, by an imino group substituted by the group $R_6$, or by a sulfinyl or sulfonyl group, whilst $R_6$ denotes a hydrogen atom, a $C_{1-4}$-alkyl, $C_{3-7}$-cycloalkyl, $C_{3-7}$-cycloalkyl-$C_{1-4}$-alkyl, formyl, $C_{1-4}$-alkylcarbonyl, $C_{1-4}$-alkylsulfonyl, aminocarbonyl, $C_{1-4}$-alkylaminocarbonyl or di-($C_{1-4}$-alkyl)-aminocarbonyl group, an imidazolyl group optionally substituted by 1 to 3 methyl groups, a $C_{5-7}$-cycloalkyl group wherein a methylene group is replaced by an oxygen or sulfur atom, by an imino group substituted by the group $R_6$, by a sulfinyl or sulfonyl group, whilst $R_6$ is as hereinbefore defined, or D together with E denotes a hydrogen, fluorine or chlorine atom, a $C_{1-4}$-alkyl group optionally substituted by 1 to 5 fluorine atoms, a $C_{3-6}$-cycloalkyl group, an aryl, heteroaryl, $C_{1-4}$-alkylcarbonyl or arylcarbonyl group, a carboxy, $C_{1-4}$-alkoxycarbonyl, aminocarbonyl, $C_{1-4}$-alkylaminocarbonyl or di-($C_{1-4}$-alkyl)-aminocarbonyl group or a carbonyl which is substituted by a 4- to 7-membered alkyleneimino group, whilst in the abovementioned 6- to 7-membered alkyleneimino groups a methylene group may in each case be replaced in the 4 position by an oxygen or sulfur atom, by an imino group substituted by the group $R_6$, by a sulfinyl or sulfonyl group, whilst $R_6$ is as hereinbefore defined, and $R_c$ denotes a $C_{4-7}$-cycloalkoxy or $C_{3-7}$-cycloalkyl-$C_{1-6}$-alkoxy group wherein the cycloalkyl moiety in each case may be substituted by a $C_{1-3}$-alkyl, hydroxy, $C_{1-4}$-alkoxy, amino, $C_{1-4}$-alkylamino, di-($C_{1-4}$-alkyl)-amino, pyrrolidino, piperidino, morpholino, piperazino, N-($C_{1-2}$-alkyl)-piperazino, hydroxy-$C_{1-2}$-alkyl, $C_{1-4}$-alkoxy-$C_{1-2}$-alkyl, amino-$C_{1-2}$-alkyl, $C_{1-4}$-alkylamino-$C_{1-2}$-alkyl, di-($C_{1-4}$-alkyl)-amino-$C_{1-2}$-alkyl, pyrrolidino-$C_{1-2}$-alkyl, piperidino-$C_{1-2}$-alkyl, morpholino-$C_{1-2}$-alkyl, piperazino-$C_{1-2}$-alkyl or N-($C_{1-2}$-alkyl)-piperazino-$C_{1-2}$-alkyl group, whilst the abovementioned monosubstituted cycloalkyl moieties may additionally be substituted by a $C_{1-3}$-alkyl group, or a 3-pyrrolidinyloxy, 2-pyrrolidinyl-$C_{1-4}$-alkyloxy, 3-pyrrolidinyl-$C_{1-4}$-alkyloxy, 3-piperidinyloxy, 4-piperidinyloxy, 2-piperidinyl-$C_{1-4}$-alkyloxy, 3-piperidinyl-$C_{1-4}$-alkyloxy, 4-piperidinyl-$C_{1-4}$-alkyloxy, 3-hexahydro-azepinyloxy, 4-hexahydro-azepinyloxy, 2-hexahydro-azepinyl-$C_{1-4}$-alkyloxy, 3-hexahydro-azepinyl-$C_{1-4}$-alkyloxy or 4-hexahydro-azepinyl-$C_{1-4}$-alkyloxy group wherein in each case the cyclic nitrogen atom is substituted by the group $R_6$, where $R_6$ is as hereinbefore defined.

By the aryl moieties mentioned in the definition of the abovementioned groups is meant a phenyl group which in each case may be monosubstituted by $R_7$, mono-, di- or trisubstituted by $R_8$ or monosubstituted by $R_7$ and additionally mono- or disubstituted by $R_8$, wherein the substituents may be identical or different and $R_7$ denotes a cyano, carboxy, $C_{1-4}$-alkoxycarbonyl, aminocarbonyl, $C_{1-4}$-alkylaminocarbonyl, di-($C_{1-4}$-alkyl)-aminocarbonyl, $C_{1-4}$-alkylsulfenyl, $C_{1-4}$-alkylsulfinyl, $C_{1-4}$-alkylsulfonyl, hydroxy, $C_{1-4}$-alkylsulfonyloxy, trifluoromethyloxy, nitro, amino, $C_{1-4}$-alkylamino, di-($C_{1-4}$-alkyl)-amino, $C_{1-4}$-alkylcarbonylamino, N-($C_{1-4}$-alkyl)-$C_{1-4}$-alkylcarbonylamino, $C_{1-4}$-alkylsulfonylamino, N-($C_{1-4}$-alkyl)-$C_{1-4}$-alkylsulfonylamino, aminosulfonyl, $C_{1-4}$-alkylaminosulfonyl or di-($C_{1-4}$-alkyl)-aminosulfonyl group or a carbonyl group which is substituted by a 5- to 7-membered alkyleneimino group, whilst in the abovementioned 6- to 7-membered alkyleneimino groups in each case a methylene group in the 4 position may be replaced by an oxygen or sulfur atom, by a sulfinyl, sulfonyl, imino or N-($C_{1-4}$-alkyl)-imino group, and $R_8$ denotes a fluorine, chlorine, bromine or iodine atom, a $C_{1-4}$-alkyl, trifluoromethyl or $C_{1-4}$-alkoxy group or two groups $R_8$, if they are bound to adjacent carbon atoms, together denote a $C_{3-5}$-alkylene, methylenedioxy or 1,3-butadien-1,4-ylene group.

The heteroaryl groups mentioned in the definition of the abovementioned groups also include a 5-membered heteroaromatic group which contains an imino group, an oxygen or sulfur atom or an imino group, an oxygen or sulfur atom and one or two nitrogen atoms, or a 6-membered heteroaromatic group which contains one, two or three nitrogen atoms, whilst the abovementioned 5-membered heteroaromatic groups may be substituted in each case by 1 or 2 methyl or ethyl groups and the abovementioned 6-membered heteroaromatic groups may be substituted in each case by 1 or 2 methyl or ethyl groups or by a fluorine, chlorine, bromine or iodine atom or by a trifluoromethyl, hydroxy, methoxy or ethoxy group.

Preferred compounds of the above general formula I are those wherein $R_a$ denotes a hydrogen atom, $R_b$ denotes a phenyl, benzyl or 1-phenylethyl group wherein the phenyl nucleus is substituted in each case by the groups $R_1$ to $R_3$, whilst $R_1$ and $R_2$, which may be identical or different, in each case denote a hydrogen, fluorine, chlorine, bromine or iodine atom, a $C_{1-4}$-alkyl, hydroxy, $C_{1-4}$-alkoxy, $C_{3-6}$-cycloalkyl, $C_{4-6}$-cycloalkoxy, $C_{2-5}$-alkenyl or $C_{2-5}$-alkynyl group, an aryl, aryloxy, arylmethyl or arylmethoxy group, a methyl or methoxy group substituted by 1 to 3 fluorine atoms, a cyano or nitro group and $R_3$ denotes a hydrogen, fluorine, chlorine or bromine atom, a $C_{1-4}$-alkyl, trifluoromethyl or $C_{1-4}$-alkoxy group, X denotes a methine group substituted by a cyano group or a nitrogen atom, A denotes an imino group, B denotes a carbonyl or sulfonyl group, C denotes a 1,3-allenylene, 1,1- or 1,2-vinylene group, an ethynylene or 1,3-butadien-1,4-ylene group, D denotes an alkylene, —CO-alkylene or —SO$_2$-alkylene group wherein the alkylene moiety in each case contains 1 to 4 carbon atoms and additionally 1 to 4 hydrogen atoms in the alkylene moiety may be replaced by fluorine atoms, whilst the linking of the —CO-alkylene or —SO$_2$-alkylene group to the adjacent group C in each case must take place via the carbonyl or sulfonyl group, a —CO—O-alkylene, —CO—NR$_4$-alkylene or —SO$_2$—NR$_4$-alkylene group wherein the alkylene moiety in each case contains 1 to 4 carbon atoms, whilst the linking to the adjacent group C in each case must take place via the carbonyl or sulfonyl group, wherein $R_4$ denotes a hydrogen atom or a $C_{1-4}$-alkyl group, or, if D is bound to a carbon atom of the group E, it may also denote a bond, or, if D is bound to a nitrogen atom of the group E, it may also denote a carbonyl or sulfonyl group, E denotes a di-($C_{1-4}$-alkyl)-amino group wherein the alkyl moieties may be identical or different, an N-($C_{1-4}$-alkyl)-N-($C_{2-4}$-alkyl)-amino group wherein the $C_{2-4}$-alkyl moiety is substituted in β-, γ-, or δ-position with regard to the nitrogen atom of the amino group by the group $R_5$, where $R_5$ denotes a hydroxy, $C_{1-4}$-alkoxy or di-($C_{1-4}$-alkyl)-amino group, a 4- to 7-membered alkyleneimino group optionally substituted by one or two methyl groups or a 6- to 7-membered alkyleneimino group optionally substituted by one or two methyl groups wherein in each case a methylene group in position 4 is replaced by an oxygen or sulfur atom, or by a sulfinyl, sulfonyl or N-($C_{1-4}$-alkyl)-imino group, a di-($C_{2-4}$-alkyl)-amino group wherein the two $C_{2-4}$-alkyl moieties in each case are substituted in β-, γ-, or δ-position with regard to the nitrogen atom of the amino group by the group $R_5$, wherein the substituents may be identical or different and $R_5$ is as hereinbefore defined, a $C_{3-7}$-cycloalkylamino or $C_{3-7}$-cycloalkyl-$C_{1-3}$-alkylamino group wherein in each case the nitrogen atom is substituted by a further $C_{1-4}$-alkyl group, a $C_{1-4}$-alkylamino group wherein the nitrogen atom is substituted by a tetrahydrofuran-3-yl, tetrahydropyran-3-yl, tetrahydropyran-4-yl, tetrahydrofuranylmethyl, 1-(tetrahydrofuran-3-yl)piperidin-4-yl, 1-(tetrahydropyran-3-yl)piperidin-4-yl, 1-(tetrahydropyran-4-yl)piperidin-4-yl, N-($C_{1-2}$-alkyl)-3-pyrrolidinyl, N-($C_{1-2}$-alkyl)-3-piperidinyl, N-($C_{1-2}$-alkyl)-4-piperidinyl, N-($C_{1-2}$-alkyl)-3-hexahydro-azepinyl or N-($C_{1-2}$-alkyl)-4-hexahydro-azepinyl group, an 4- to 7-membered alkyleneimino group optionally substituted by 1 to 4 methyl groups, which may be substituted either at a cyclic carbon atom or at one of the methyl groups by the group $R_5$, where $R_5$ is as hereinbefore defined, a piperidino group substituted by a tetrahydrofuranyl, tetrahydropyranyl or tetrahydrofuranylmethyl group, a 6- to 7-membered alkyleneimino group optionally substituted by 1 or 2 methyl groups wherein in each case a methylene group is replaced in the 4 position by an oxygen or sulfur atom, by an imino group substituted by the group $R_6$, by a sulfinyl or sulfonyl group, whilst $R_6$ denotes a $C_{1-4}$-alkyl, 2-methoxyethyl, 3-methoxypropyl, $C_{3-7}$-cycloalkyl, $C_{3-7}$-cycloalkyl-$C_{1-4}$-alkyl, tetrahydrofuran-3-yl, tetrahydropyran-3-yl, tetrahydropyran-4-yl, tetrahydrofuranylmethyl, formyl, $C_{1-4}$-alkylcarbonyl, $C_{1-4}$-alkylsulfonyl, aminocarbonyl, $C_{1-4}$-alkylaminocarbonyl or di-($C_{1-4}$-alkyl)-aminocarbonyl group, a $C_{5-7}$-cycloalkyl group wherein a methylene group is replaced by an oxygen or sulfur atom, by an imino group substituted by the group $R_6$, or by a sulfinyl or sulfonyl group, where $R_6$ is as hereinbefore defined, or D together with E denotes a hydrogen, fluorine or chlorine atom, a $C_{1-4}$-alkyl group optionally substituted by 1 to 5 fluorine atoms, a $C_{3-6}$-cycloalkyl group, an aryl, $C_{1-4}$-alkylcarbonyl or arylcarbonyl group, a carboxy, $C_{1-4}$-alkoxycarbonyl, aminocarbonyl, $C_{1-4}$-alkylaminocarbonyl or di-($C_{1-4}$-alkyl)-aminocarbonyl group or a carbonyl group which is substituted by a 4- to 7-membered alkyleneimino group, whilst in the abovementioned 6- to 7-membered alkyleneimino groups in each case a methylene group in the 4 position may be replaced by an oxygen or sulfur atom, by an imino group substituted by the group $R_6$, or by a sulfinyl or sulfonyl group, where $R_6$ is as hereinbefore defined, and $R_c$ denotes a $C_{4-7}$-cycloalkoxy or $C_{3-7}$-cycloalkyl-$C_{1-6}$-alkoxy group wherein the cycloalkyl moiety in each case may be substituted by a $C_{1-3}$-alkyl, hydroxy, $C_{1-4}$-alkoxy, di-($C_{1-4}$-alkyl)-amino, pyrrolidino, piperidino, morpholino, N-($C_{1-2}$-alkyl)-piperazino, hydroxy-$C_{1-2}$-alkyl, $C_{1-4}$-alkoxy-$C_{1-2}$-alkyl, di-($C_{1-4}$-alkyl)-amino-$C_{1-2}$-alkyl, pyrrolidino-$C_{1-2}$-alkyl, piperidino-$C_{1-2}$-alkyl, morpholino-$C_{1-2}$-alkyl or N-($C_{1-2}$-alkyl)-piperazino-$C_{1-2}$-alkyl group, whilst the abovementioned monosubstituted cycloalkyl moieties may additionally be substituted by a $C_{1-3}$-alkyl group, a tetrahydrofuran-3-yloxy, tetrahydropyran-3-yloxy, tetrahydropyran-4-yloxy or tetrahydrofuranylmethoxy group, an $C_{2-4}$-alkoxy group substituted in β-, γ-, or δ-position with regard to the oxygen atom by an azetidin-1-yl, 4-methyl-homopiperazino or 4-ethyl-homopiperazino group, a 3-pyrrolidinyloxy, 2-pyrrolidinyl-$C_{1-4}$-alkyloxy, 3-pyrrolidinyl-$C_{1-4}$-alkyloxy, 3-piperidinyloxy, 4-piperidinyloxy, 2-piperidinyl-$C_{1-4}$-alkyloxy, 3-piperidinyl-$C_{1-4}$-alkyloxy, 4-piperidinyl-$C_{1-4}$-alkyloxy, 3-hexahydro-azepinyloxy, 4-hexahydro-azepinyloxy, 2-hexahydro-azepinyl-$C_{1-4}$-alkyloxy, 3-hexahydro-azepinyl-$C_{1-4}$-alkyloxy or 4-hexahydro-azepinyl-$C_{1-4}$-alkyloxy group wherein in each case the cyclic nitrogen atom is substituted by the group $R_6$, where $R_6$ is as hereinbefore defined, whilst by the aryl moieties mentioned in the definition of the abovementioned groups is meant a phenyl group which may in each case be monosubstituted by $R_7$, mono-, di- or trisubstituted by $R_8$ or monosubstituted by $R_7$ and additionally mono- or disubstituted by $R_8$, wherein the substituents may be identical or different and $R_7$ denotes a cyano, carboxy, $C_{1-4}$-alkoxycarbonyl, aminocarbonyl, $C_{1-4}$-alkylaminocarbonyl, di-($C_{1-4}$-alkyl)-aminocarbonyl, $C_{1-4}$-alkylsulfenyl, $C_{1-4}$-alkylsulfinyl, $C_{1-4}$-alkylsulfonyl, hydroxy, $C_{1-4}$-alkylsulfonyloxy, trifluoromethyloxy, nitro, amino, $C_{1-4}$-alkylamino, di-($C_{1-4}$-alkyl)-amino, $C_{1-4}$-alkylcarbonylamino, N-($C_{1-4}$-alkyl)-$C_{1-4}$-alkylcarbonylamino, $C_{1-4}$-alkylsulfonylamino, N-($C_{1-4}$-alkyl)-$C_{1-4}$-alkylsulfonylamino, aminosulfonyl, $C_{1-4}$-alkylaminosulfonyl or di-($C_{1-4}$-alkyl)-aminosulfonyl group or a carbonyl group which is substituted by a 5- to 7-membered alkyleneimino group, whilst in the abovementioned 6- to 7-membered alkyleneimino groups in each case a methylene group may be replaced in the 4 position by an oxygen or sulfur atom, by a sulfinyl, sulfonyl, imino or N-($C_{1-4}$-alkyl)-imino group, and $R_8$ denotes a fluorine, chlorine, bromine or iodine atom, a $C_{1-4}$-alkyl, trifluoromethyl or $C_{1-4}$-alkoxy group or two groups $R_8$, if they are bound to adjacent carbon atoms, together denote a $C_{3-5}$-alkylene, methylenedioxy or 1,3-butadien-1,4-ylene group, the tautomers, stereoisomers and salts thereof.

Particularly preferred compounds of the above general formula I are those wherein $R_a$ denotes a hydrogen atom, $R_b$ denotes a phenyl, benzyl or 1-phenylethyl group wherein the phenyl nucleus is substituted in each case by the groups $R_1$ and $R_2$, where $R_1$ and $R_2$, which may be identical or different, in each case denote a hydrogen, fluorine, chlorine or bromine atom, a methyl, trifluoromethyl or methoxy group, X denotes a nitrogen atom, A denotes an imino group, B denotes a carbonyl group, C denotes a 1,2-vinylene group, an ethynylene or 1,3-butadien-1,4-ylene group, D denotes a $C_{1-4}$-alkylene group, or, if D is bound to a carbon atom of the group E, it may also denote a bond, or, if D is bound to a nitrogen atom of the group E, it may also denote a carbonyl group, E denotes a di-($C_{1-4}$-alkyl)-amino group wherein the alkyl moieties may be identical or different, an N-($C_{1-4}$-alkyl)-N-($C_{2-4}$-alkyl)-amino group wherein the $C_{2-4}$-alkyl moiety is substituted in β-, γ-, or δ-position with regard to the nitrogen atom of the amino group by the group $R_5$, whilst $R_5$ denotes a hydroxy, $C_{1-3}$-alkoxy or di-($C_{1-3}$-alkyl)-amino group, a pyrrolidino, piperidino or morpholino group, a di-($C_{2-4}$-alkyl)-amino group wherein the two $C_{2-4}$-alkyl moieties in each case are substituted in β-, γ-, or δ-position with regard to the nitrogen atom of the amino group by the group $R_5$, wherein the substituents may be identical or different and $R_5$ is as hereinbefore defined, an $C_{1-4}$-alkylamino group substituted at the nitrogen atom by a tetrahydrofuran-3-yl, tetrahydropyran-3-yl, tetrahydropyran-4-yl, tetrahydrofuranylmethyl, 1-($C_{1-2}$-alkyl)-pyrrolidin-3-yl, 1-($C_{1-2}$-alkyl)-piperidin-3-yl, 1-($C_{1-2}$-alkyl)-piperidin-4-yl, 1-(tetrahydrofuran-3-yl)piperidin-4-yl, 1-(tetrahydropyran-3-yl)piperidin-4-yl or 1-(tetrahydropyran-4-yl)piperidin-4-yl group, a $C_{3-5}$-cycloalkylamino or $C_{3-5}$-cycloalkyl-$C_{1-3}$-alkylamino group wherein in each case the nitrogen atom is substituted by a further $C_{1-3}$-alkyl group, a 5- to 7-membered alkyleneimino group optionally substituted by 1 or 2 methyl groups which may be substituted either at a cyclic carbon atom or at one the methyl groups by the group $R_5$, where $R_5$ is as hereinbefore defined, or a piperidino group substituted by a tetrahydrofuranyl, tetrahydropyranyl or tetrahydrofuranylmethyl group, a piperidino group optionally substituted by 1 or 2 methyl groups wherein the methylene group is replaced in the 4 position by an oxygen or sulfur atom, by sulfinyl or sulfonyl group or by an imino group substituted by the group $R_6$, whilst $R_6$ denotes a $C_{1-3}$-alkyl, 2-methoxyethyl, 3-methoxypropyl, $C_{3-6}$-cycloalkyl, $C_{3-6}$-cycloalkyl-$C_{1-3}$-alkyl, tetrahydrofuran-3-yl, tetrahydropyran-3-yl, tetrahydropyran-4-yl, tetrahydrofuranylmethyl, $C_{1-3}$-alkylcarbonyl, $C_{1-3}$-alkylsulfonyl, aminocarbonyl, $C_{1-3}$-alkylaminocarbonyl or di-($C_{1-3}$-alkyl)-aminocarbonyl group, or D together with E denotes a hydrogen atom,
a $C_{1-3}$-alkyl group,
an aryl or $C_{1-4}$-alkylcarbonyl group or
a $C_{1-4}$-alkoxycarbonyl group, $R_c$ denotes a $C_{4-7}$-cycloalkoxy or $C_{3-7}$-cycloalkyl-$C_{1-4}$-alkoxy group wherein the cycloalkyl moiety in each case may be substituted by a $C_{1-3}$-alkyl or $C_{1-3}$-alkoxy group, a tetrahydrofuran-3-yloxy, tetrahydropyran-3-yloxy, tetrahydropyran-4-yloxy or tetrahydrofuranylmethoxy group, an $C_{2-4}$-alkoxy group substituted in β-, γ-, or δ-position with regard to the oxygen atom by an azetidin-1-yl, 4-methyl-homopiperazino or 4-ethyl-homopiperazino group, a 3-pyrrolidinyloxy, 2-pyrrolidinyl-$C_{1-3}$-alkyloxy, 3-pyrrolidinyl-$C_{1-3}$-alkyloxy, 3-piperidinyloxy, 4-piperidinyloxy, 2-piperidinyl-$C_{1-3}$-alkyloxy, 3-piperidinyl-$C_{1-3}$-alkyloxy, 4-piperidinyl-$C_{1-3}$-alkyloxy, 3-hexahydro-azepinyloxy, 4-hexahydro-azepinyloxy, 2-hexahydro-azepinyl-$C_{1-3}$-alkyloxy, 3-hexahydro-azepinyl-$C_{1-3}$-alkyloxy or 4-hexahydro-azepinyl-$C_{1-3}$-alkyloxy group wherein in each case the cyclic nitrogen atom is substituted by a methyl or ethyl group, whilst by the aryl moieties mentioned in the definition of the abovementioned groups is meant a phenyl group which may be mono-, di- or trisubstituted by $R_8$, wherein the substituents may be identical or different and $R_8$ denotes a fluorine, chlorine, bromine or iodine atom, a $C_{1-4}$-alkyl, trifluoromethyl or $C_{1-4}$-alkoxy group, the tautomers, stereoisomers and salts thereof.

Most particularly preferred compounds of the above general formula I are those wherein $R_a$ denotes a hydrogen atom, $R_b$ denotes a phenyl, benzyl or 1-phenylethyl group, whilst the phenyl nucleus is substituted in each case by the radicals $R_1$ and $R_2$, whilst $R_1$ and $R_2$, which may be identical or different, each denotes a hydrogen, fluorine, chlorine or bromine atom, X denotes a nitrogen atom, A denotes an imino group, B denotes a carbonyl group, C denotes a 1,2-vinylene, ethinylene or 1,3-butadien-1,4-ylene group, D denotes an $C_{1-3}$-alkylene group, E denotes a Di-($C_{1-4}$-alkyl)-amino group, wherein the alkyl moieties may be identical or different, a methylamino or ethylamino group each substituted at the nitrogen atom by a 2-methoxyethyl, 1-methoxy-2-propyl, 2-methoxypropyl, 3-methoxypropyl, tetrahydrofuran-3-yl, tetrahydropyran-4-yl, tetrahydrofuran-2-ylmethyl, 1-methylpiperidin-4-yl, 1-ethylpiperidin-4-yl, 1-(tetrahydrofuran-3-yl)piperidin-4-yl, cyclopropyl or cyclopropylmethyl group, a Bis-(2-methoxyethyl)amino group, a pyrrolidino, piperidino or morpholino group each optionally substituted by one or two methyl groups, a piperazino group substituted in 4-position by a methyl, ethyl, cyclopropyl, cyclopropylmethyl, 2-methoxyethyl, tetrahydrofuran-3-yl, tetrahydropyran-4-yl or tetrahydrofuran-2-ylmethyl group, a thiomorpholino, S-oxidothiomorpholino or S,S-dioxidothiomorpholino group, a 2-(methoxymethyl)pyrrolidino, 2-(ethoxymethyl)pyrrolidino, 4-hydroxypiperidino, 4-methoxypiperidino, 4-ethoxypiperidino, 4-(tetrahydrofuran-3-yl)piperidino or 4-morpholinopiperidino group or D together with E denote a hydrogen atom, a methyl, phenyl, methoxycarbonyl or ethoxycarbonyl group and $R_c$ denotes a cyclopropylmethoxy, cyclobutylmethoxy, cyclopentylmethoxy or cyclohexylmethoxy group, a cyclobutyloxy, cyclopentyloxy or cyclohexyloxy group, a tetrahydrofuran-3-yloxy, tetrahydropyran-4-yloxy or tetrahydrofuran-2-ylmethoxy group, a straight chained $C_{2-4}$-alkoxy group terminally substituted by an azetidin-1-yl, 4-methyl-homopiperazino or 4-ethyl-homopiperazino group, a 1-methylpiperidin-4-yloxy or 1-ethylpiperidin-4-yloxy group, a (1-methylpiperidin-4-yl)-$C_{1-3}$-alkyloxy or (1-ethylpiperidin-4-yl)-$C_{1-3}$-alkyloxy group, especially those compounds wherein $R_a$ denotes a hydrogen atom, $R_b$ denotes a 1-phenylethyl group or a phenyl group wherein the phenyl nucleus is substituted by the radicals $R_1$ and $R_2$, whilst $R_1$ and $R_2$, which may be identical or different, each denote a hydrogen, fluorine, chlorine or bromine atom, X denotes a nitrogen atom, A denotes an imino group, B denotes a carbonyl group, C denotes a 1,2-vinylene, ethinylene or 1,3-butadien-1,4-ylene group, D denotes a methylene group, E denotes a dimethylamino, diethylamino, bis(2-methoxyethyl)amino, N-methyl-N-(2-methoxyethyl)amino, N-ethyl-N-(2-methoxyethyl)amino, N-methyl-N-cyclopropyl-amino, N-methyl-N-cyclopropylmethyl-amino, N-methyl-N-(1-methoxy-2-propyl)amino, N-methyl-N-(2-methoxypropyl)amino, N-methyl-N-(3-methoxypropyl)amino-, N-methyl-N-(tetrahydrofuran-3-yl)amino, N-methyl-N-(tetrahydropyran-4-yl)amino, N-methyl-N-(tetrahydrofuran-2-ylmethyl)amino or N-methyl-N-(1-methylpiperidin-4-yl) amino group, a pyrrolidino, piperidino or morpholino group each optionally substituted by one or two methyl groups, a piperazino group substituted in 4-position by a methyl, ethyl, cyclopropylmethyl or 2-methoxyethyl group, a S-oxidothiomorpholino group, a 2-(methoxymethyl)pyrrolidino, 4-hydroxypiperidino or 4-methoxypiperidino group or D together with E denote a hydrogen atom, a methyl, phenyl or ethoxycarbonyl group, and $R_c$ denotes a cyclopropylmethoxy, cyclobutyloxy or cyclopentyloxy group, a tetrahydrofuran-3-yloxy, tetrahydropyran-4-yloxy or tetrahydrofuran-2-ylmethoxy group, a straight chained $C_{2-4}$-alkoxy group terminally substituted by an azetidin-1-yl or 4-methyl-homopiperazino group, a 1-methylpiperidin-4-yloxy group or a (1-methylpiperidin-4-yl)-$C_{1-3}$-alkyloxy group, the tautomers, stereoisomers and salts thereof.

The following particularly valuable compounds of general formula I may be mentioned by way of example:

(a) 4-[(3-Chloro-4-fluorophenyl)amino]-7-[3-(1-methylpiperidin-4-yl)propyloxy]-6-[(vinylcarbonyl)amino] quinazoline, (b) 4-[(3-Chloro-4-fluorophenyl)amino]-6-{[4-(N,N-diethylamino)-1-oxo-2-buten-1-yl]amino}-7-cyclopropylmethoxyquinazoline and (c) 4-[(3-Chloro-4-fluorophenyl)amino]-6-{[4-(morpholin-4-yl)-1-oxo-2-buten-1-yl]amino}-7-cyclopropylmethoxyquinazoline as well as the salts thereof.

The compounds of general formula I may be prepared, for example, by the following processes:

a) reacting a compound of general formula

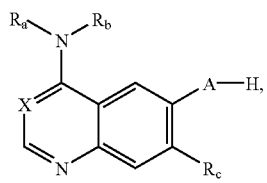

(II)

$R_a$ to $R_c$, A and X are as hereinbefore defined, with a compound of general formula $Z_1$-B-C-D-E  (III)

wherein

B to E are as hereinbefore defined and $Z_1$ denotes a leaving group such as a halogen atom, e.g., a chlorine or bromine atom, or a hydroxy group.

The reaction is optionally carried out in a solvent or mixture of solvents such as methylene chloride, dimethylformamide, benzene, toluene, chlorobenzene, tetrahydrofuran, benzene/-tetrahydrofuran or dioxane optionally in the presence of an inorganic or organic base and optionally in the presence of a dehydrating agent, expediently at temperatures between –50° C. and 150° C., preferably at temperatures between –20° C. and 80° C.

With a compound of general formula III wherein $Z_1$ denotes a leaving group, the reaction is optionally carried out in a solvent or mixture of solvents such as methylene chloride, dimethylformamide, benzene, toluene, chlorobenzene, tetrahydrofuran, benzene/tetrahydrofuran or dioxane conveniently in the presence of a tertiary organic base such as triethylamine, pyridine or 2-dimethylaminopyridine, in the presence of N-ethyl-diisopropylamine (Hünig base), whilst these organic bases may simultaneously also act as solvent, or in the presence of an inorganic base such as sodium carbonate, potassium carbonate or sodium hydroxide solution expediently at temperatures between –50° C. and 150° C., preferably at temperatures between –20° C. and 80° C.

With a compound of general formula III wherein $Z_1$ denotes a hydroxy group, the reaction is preferably carried out in the presence of a dehydrating agent, e.g., in the presence of isobutyl chloroformate, thionyl chloride, trimethyl chlorosilane, phosphorus trichloride, phosphorus pentoxide, hexamethyldisilazane, N,N'-dicyclohexylcarbodiimide, N,N'-dicyclohexylcarbodiimide/N-hydroxysuccinimide or 1-hydroxybenzotriazole and optionally also in the presence of 4-dimethylamino-pyridine, N,N'-carbonyldiimidazole or triphenylphosphine/carbon tetrachloride, expediently in a solvent such as methylene chloride, tetrahydrofuran, dioxane, toluene, chlorobenzene, dimethylsulfoxide, ethylene glycol monomethylether, ethylene glycol, diethylether or sulfolane and optionally in the presence of a reaction accelerator such as 4-dimethylaminopyridine at temperatures between –50° C. and 150° C., but preferably at temperatures between –20° C. and 80° C.

b) In order to prepare compounds of general formula I wherein the group E is linked to the group D via a nitrogen atom:

reacting a compound of general formula

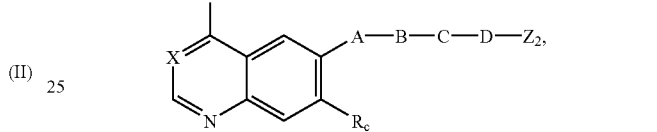

(IV)

$R_a$ to $R_c$, A to D and X are as hereinbefore defined and $Z_2$ denotes a leaving group such as a halogen atom, a substituted hydroxy or sulfonyloxy group such as a chlorine or bromine atom, a methanesulfonyloxy or p-toluenesulfonyloxy group, with a compound of general formula

H-E'  (V)

wherein

E' denotes one of the groups mentioned for E hereinbefore, which is linked to the group D via a nitrogen atom.

The reaction is expediently carried out in a solvent such as isopropanol, butanol, tetrahydrofuran, dioxane, toluene, chlorobenzene, dimethylformamide, dimethylsulfoxide, methylene chloride, ethylene glycol monomethylether, ethylene glycol diethylether or sulfolane, optionally in the presence of an inorganic or tertiary organic base, e.g., sodium carbonate or potassium hydroxide, a tertiary organic base, e.g., triethylamine, or in the presence of N-ethyldiisopropylamine (Hünig base), whilst these organic bases may simultaneously also serve as solvent, and optionally in the presence of a reaction accelerator such as an alkali metal halide at temperatures between –20° C. and 150° C., but preferably at temperatures between –10° C. and 100° C. The reaction may, however, also be carried out without a solvent or in an excess of the compound of general formula V used.

If according to the invention a compound of general formula I is obtained which contains an amino, alkylamino or imino group, this may be converted by acylation or sulfonylation into a corresponding acyl or sulfonyl compound of general formula I or if a compound of general formula I is obtained which contains an amino, alkylamino or imino group, this may be converted by alkylation or reductive alkylation into a corresponding alkyl compound of general formula I or if a compound of general formula I is obtained which contains a carboxy or hydroxyphosphoryl group, this may be converted by esterification into a corresponding ester of general formula I or if a compound of general formula I is obtained which contains a carboxy or ester group, this may be converted by reaction with an amine into a corresponding amide of general formula I.

The subsequent esterification is optionally carried out in a solvent or mixture of solvents such as methylene chloride, dimethylformamide, benzene, toluene, chlorobenzene, tetrahydrofuran, benzene/tetrahydrofuran or dioxane or most advantageously in a corresponding alcohol, optionally in the presence of an acid such as hydrochloric acid or in the presence of a dehydrating agent, e.g., in the presence of isobutyl chloroformate, thionyl chloride, trimethylchlorosilane, sulfuric acid, methanesulfonic acid, p-toluenesulfonic acid, phosphorus trichloride, phosphorus pentoxide, N,N'-dicyclohexylcarbodiimide, N,N'-dicyclohexylcarbodiimide/N-hydroxysuccinimide or 1-hydroxybenzotriazole and optionally additionally in the presence of 4-dimethylamino-pyridine, N,N'-carbonyldiimidazole or triphenylphosphine/carbon tetrachloride, conveniently at temperatures between 0° C. and 150° C., preferably at temperatures between 0° C. and 80° C.

The subsequent ester formation may also be carried out by reacting a compound which contains a carboxy or hydroxy-phosphoryl group with a corresponding alkyl halide.

The subsequent acylation or sulfonylation is conveniently carried out in a solvent or mixture of solvents such as methylene chloride, dimethylformamide, benzene, toluene, chlorobenzene, tetrahydrofuran, benzene/tetrahydrofuran or dioxane with a corresponding acyl or sulfonyl derivative optionally in the presence of a tertiary organic base or in the presence of an inorganic base or in the presence of a dehydrating agent, e.g., in the presence of isobutyl chloroformate, thionyl chloride, trimethylchlorosilane, sulfuric acid, methanesulfonic acid, p-toluenesulfonic acid, phosphorus trichloride, phosphorus pentoxide, N,N'-dicyclohexylcarbodiimide, N,N'-dicyclohexylcarbodiimide/N-hydroxysuccinimide or 1-hydroxybenzotriazole and optionally also in the presence of 4-dimethylamino-pyridine, N,N'-carbonyldiimidazole or triphenylphosphine/carbon tetrachloride, expediently at temperatures between 0° C. and 150° C., preferably at temperatures between 0° C. and 80° C.

The subsequent alkylation is optionally carried out in a solvent or mixture of solvents such as methylene chloride, dimethylformamide, benzene, toluene, chlorobenzene, tetrahydrofuran, benzene/tetrahydrofuran or dioxane with an alkylating agent such as a corresponding halide or sulfonic acid ester, e.g., with methyl iodide, ethyl bromide, dimethyl sulfate or benzyl chloride, optionally in the presence of a tertiary organic base or in the presence of an inorganic base, expediently at temperatures between 0° C. and 150° C., preferably at temperatures between 0° C. and 100° C.

The subsequent reductive alkylation is carried out with a corresponding carbonyl compound such as formaldehyde, acetaldehyde, propionaldehyde, acetone or butyraldehyde in the presence of a complex metal hydride such as sodium borohydride, lithium borohydride, sodium triacetoxyborohydride or sodium cyanoborohydride, expediently at a pH of 6–7 and at ambient temperature or in the presence of a hydration catalyst, e.g., with hydrogen in the presence of palladium/charcoal, at a hydrogen pressure of 1 to 5 bar. The methylation can also be carried out in the presence of formic acid as reduction agent at elevated temperatures, e.g., at temperatures between 60° C. and 120° C.

The subsequent amide formation is carried out by reacting a corresponding reactive carboxylic acid derivative with a corresponding amine, optionally in a solvent or mixture of solvents such as methylene chloride, dimethylformamide, benzene, toluene, chlorobenzene, tetrahydrofuran, benzene/tetrahydrofuran or dioxane, whilst the amine used may simultaneously serve as solvent, optionally in the presence of a tertiary organic base or in the presence of an inorganic base or with a corresponding carboxylic acid in the presence of a dehydrating agent, e.g., in the presence of isobutyl chloroformate, thionyl chloride, trimethylchlorosilane, phosphorus trichloride, phosphorus pentoxide, N,N'-dicyclohexylcarbodiimide, N,N'-dicyclohexylcarbodiimide/N-hydroxysuccinimide or 1-hydroxybenzotriazole and optionally also in the presence of 4-dimethylaminopyridine, N,N'-carbonyldiimidazole or triphenylphosphine/carbon tetrachloride, expediently at temperatures between 0° C. and 150° C., preferably at temperatures between 0 and 80° C.

In the reactions described hereinbefore, any reactive groups present such as hydroxy, carboxy, phosphono, O-alkyl-phosphono, amino, alkylamino or imino groups may be protected during the reaction by conventional protecting groups which are cleaved again after the reaction.

For example, a protecting group for a hydroxy group may be a trimethylsilyl, acetyl, benzoyl, methyl, ethyl, tert-butyl, trityl, benzyl or tetrahydropyranyl group, protecting groups for a carboxy group may be a trimethylsilyl, methyl, ethyl, tert-butyl, benzyl or tetrahydropyranyl group, protecting groups for a phosphono group may be an alkyl group such as the methyl, ethyl, isopropyl or n-butyl group, the phenyl or benzyl group, and protecting groups for an amino, alkylamino or imino group may be a formyl, acetyl, trifluoroacetyl, ethoxycarbonyl, tert-butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g., in water, isopropanol/water, acetic acid/water, tetrahydrofuran/water or dioxane/water, in the presence of an acid such as trifluoroacetic acid, hydrochloric acid or sulfuric acid or in the presence of an alkali metal base such as sodium hydroxide or potassium hydroxide or aprotically, e.g., in the presence of iodotrimethylsilane, at temperatures between 0° C. and 120° C., preferably at temperatures between 10° C. and 100° C.

However, a benzyl, methoxybenzyl or benzyloxycarbonyl group is cleaved, for example hydrogenolytically, e.g., with hydrogen in the presence of a catalyst such as palladium/charcoal in a suitable solvent such as methanol, ethanol, ethyl acetate or glacial acetic acid, optionally with the addition of an acid such as hydrochloric acid at temperatures between 0° C. and 100° C., but preferably at temperatures between 20° C. and 60° C., and at a hydrogen pressure of 1 to 7 bar, but preferably 3 to 5 bar. A 2,4-dimethoxybenzyl group, however, is preferably cleaved in trifluoroacetic acid in the presence of anisole.

A tert-butyl or tert-butyloxycarbonyl group is preferably cleaved by treating with an acid such as trifluoroacetic acid or hydrochloric acid or by treating with iodotrimethylsilane optionally using a solvent such as methylene chloride, dioxane, methanol or diethyl ether.

A trifluoroacetyl group is preferably cleaved by treating with an acid such as hydrochloric acid, optionally in the presence of a solvent such as acetic acid at temperatures between 50° C. and 120° C. or by treating with sodium hydroxide solution optionally in the presence of a solvent such as tetrahydrofuran at temperatures between 0° C. and 50° C.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20° C. and 50° C.

A single alkyl group may be cleaved from an O,O'-dialkylphosphono group with sodium iodide, for example, in a solvent such as acetone, methyl ethyl ketone, acetonitrile or dimethylformamide at temperatures between 40° C. and 150° C., but preferably at temperatures between 60° C. and 100° C.

Both alkyl groups may be cleaved from an O,O'-dialkylphosphono group with iodotrimethylsilane, bromotrimethylsilane or chlorotrimethylsilane/sodium iodide, for example, in a solvent such as methyl chloride, chloroform or acetonitrile at temperatures between 0° C. and the boiling temperature of the reaction mixture, but preferably at temperatures between 20° C. and 60° C.

Moreover, the compounds of general formula I obtained may be resolved into their enantiomers and/or diastereomers, as mentioned hereinbefore. Thus, for example, cis-ltrans mixtures may be resolved into their cis and trans isomers, and compounds with at least one optically active carbon atom may be separated into their enantiomers.

Thus, for example, the cis/trans mixtures may be resolved by chromatography into the cis and trans isomers thereof, the compounds of general formula I obtained which occur as racemates may be separated by methods known per se (cf. N. L. Allinger and E. L. Eliel in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g., by chromatography and/or fractional crystallization, and, if these compounds are obtained in racemic form, they may subsequently be resolved into the enantiomers as mentioned above.

The enantiomers are preferably separated by column separation on chiral phases or by recrystallization from an optically active solvent or by reacting with an optically active substance which forms salts or derivatives such as e.g., esters or amides with the racemic compound, particularly acids and the activated derivatives or alcohols thereof, and separating the diastereomeric mixture of salts or derivatives thus obtained, e.g., on the basis of their differences in solubility, whilst the free antipodes may be released from the pure diastereomeric salts or derivatives by the action of suitable agents. Optically active acids in common use are e.g., the D- and L-forms of tartaric acid or dibenzoyltartaric acid, di-o-tolyltartaric acid, malic acid, mandelic acid, camphorsulfonic acid, glutamic acid, aspartic acid or quinic acid. An optically active alcohol may be for example (+) or (−)-menthol and an optically active acyl group in amides, for example, may be a (+)-or (−)-menthyloxycarbonyl.

Furthermore, the compounds of formula I may be converted into the salts thereof, particularly for pharmaceutical use into the physiologically acceptable salts with inorganic or organic acids. Acids which may be used for this purpose include for example hydrochloric acid, hydrobromic acid, sulfuric acid, phosphoric acid, fumaric acid, succinic acid, lactic acid, citric acid, tartaric acid or maleic acid.

Moreover, if the new compounds of formula I thus obtained contain a carboxy, hydroxyphosphoryl, sulfo or 5-tetrazolyl group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, arginine, cyclohexylamine, ethanolamine, diethanolamine and triethanolamine.

The compounds of general formulae II to V used as starting materials are known from the literature in some cases or may be obtained by methods known from the literature (cf. Examples I to VII).

For example, a starting compound of general formula I is obtained by reacting a 7-fluoro-6-nitro compound correspondingly substituted in the 4 position with a corresponding alkoxide and subsequently reducing the nitro compound thus obtained or a starting compound of general formula IV is obtained by reacting a 7-fluoro-6-nitro compound correspondingly substituted in the 4 position with a corresponding alkoxide, subsequently reducing the nitro compound thus obtained and then acylating with a corresponding compound.

As already mentioned hereinbefore, the compounds of general formula I according to the invention and the physiologically acceptable salts thereof have valuable pharmacological properties, particularly an inhibiting effect on signal transduction mediated by the Epidermal Growth Factor receptor (EGF-R), whilst this may be achieved for example by inhibiting ligand bonding, receptor dimerization or tyrosine kinase itself. It is also possible to block the transmission of signals to components located further down.

The biological properties of the new compounds were investigated as follows:

The inhibition of the EGF-R-mediated signal transmission can be demonstrated e.g., with cells which express human EGF-R and whose survival and proliferation depend on stimulation by EGF or TGF-alpha. A cell line of murine origin dependent on interleukin-3-(IL-3) which was genetically modified to express functional human EGF-R was used here. The proliferation of these cells known as F/L-HERc can therefore be stimulated either by murine IL-3 or by EGF (cf. T. von Rüden et al., EMBO J. 7, 2749–2756 (1988) and J. H Pierce et al., Science 239, 628–631 (1988)).

The starting material used for the F/L-HERc cells was the cell line FDC-$P_1$, the production of which has been described by T. M. Dexter et al., J. Exp. Med. 152, 1036–1047 (1980). Alternatively, however, other growth-factor-dependent cells may also be used (cf., for example, J. H. Pierce et al., Science 239, 628–631 (1988); H. Shibuya et al., Cell 70, 57–67 (1992); and W. S. Alexander et al., EMBO J. 10, 3683–3691 (1991)). For expressing the human EGF-R cDNA (cf. Ullrich, A. et al. in Nature 309, 418–425 (1984)) recombinant retroviruses were used as described by T. von Rüden et al., EMBO J. 7, 2749–2756 (1988), except that the retroviral vector LXSN (cf. A. D. Miller et al., BioTechniques 7, 980–990 (1989)) was used for the expression of the EGF-R cDNA and the line GP+E86 (cf. D. Markowitz et al., J. Virol. 62, 1120–1124 (1988)) was used as the packaging cell.

The test was performed as follows:

F/L-HERc cells were cultivated in RPMI/1640 medium (BioWhittaker), supplemented with 10% fetal calf serum (FCS, Boehringer Mannheim), 2 mM glutamine (BioWhittaker), standard antibiotics and 20 ng/ml of human EGF (Promega), at 37° C. and 5% $CO_2$. In order to investigate the inhibitory activity of the compounds according to the invention, $1.5 \times 10^4$ cells per well were cultivated in triplicate in 96-well dishes in the above medium (200 μl), the cell proliferation being stimulated with either EGF (20 ng/ml) or murine IL-3. The IL-3 used was obtained from culture supernatants of the cell line X63/0 mIL-3 (cf. H. Karasuyama et al., Eur. J. Immunol. 18, 97–104 (1988)). The compounds according to the invention were dissolved in 100% dimethylsulfoxide (DMSO) and added to the cultures in various dilutions, the maximum DMSO concentration being 1%. The cultures were incubated for 48 hours at 37° C.

In order to determine the inhibitory activity of the compounds according to the invention the relative cell number was measured in O.D. units using the Cell Titer 96™ Aqueous Non-Radioactive Cell Proliferation Assay (Promega). The relative cell number was calculated as a percentage of the control (F/LHERc cells without inhibitor) and the concentration of active substance which inhibits the proliferation of the cells by 50% ($IC_{50}$) was derived therefrom.

The following results were obtained:

| Compound (Example No.) | Inhibition of EGF-Dependent Proliferation $IC_{50}$ [nM] |
| --- | --- |
| 1 | <0.35 |
| 2(3) | 0.35 |
| 1(7) | <0.5 |
| 3 | 5 |
| 3(1) | 0.2 |

The compounds of general formula I according to the invention thus inhibit signal transduction by tyrosine kinases, as demonstrated by the example of the human EGF receptor, and are therefore useful for treating pathophysiological processes caused by hyperfunction of tyrosine kinases. These are e.g., benign or malignant tumors, particularly tumors of epithelial and neuroepithelial origin, metastasization and the abnormal proliferation of vascular endothelial cells (neoangiogenesis).

The compounds according to the invention are also useful for preventing and treating diseases of the airways and lungs which are accompanied by increased or altered production of mucus caused by stimulation by tyrosine kinases, e.g., in inflammatory diseases of the airways such as chronic bronchitis, chronic obstructive bronchitis, asthma, bronchiectasis, allergic or non-allergic rhinitis or sinusitis, cystic fibrosis, $\alpha_1$-antitrypsin deficiency, or coughs, pulmonary emphysema, pulmonary fibrosis and hyperreactive airways.

The compounds are also suitable for treating diseases of the gastrointestinal tract and bile duct and gall bladder which are associated with disrupted activity of the tyrosine kinases, such as may be found e.g., in chronic inflammatory changes such as cholecystitis, Crohns' disease, ulcerative colitis, and ulcers in the gastrointestinal tract or such as may occur in diseases of the gastrointestinal tract which are associated with increased secretions, such as Ménétrier's disease, secreting adenomas and protein loss syndrome.

In addition, the compounds of general formula I and the physiologically acceptable salts thereof may be used to treat other diseases caused by abnormal function of tyrosine kinases, such as e.g., epidermal hyperproliferation (psoriasis), inflammatory processes, diseases of the immune system, hyperproliferation of hematopoietic cells, etc.

By reason of their biological properties the compounds according to the invention may be used on their own or in conjunction with other pharmacologically active compounds, for example in tumour therapy, in monotherapy or in conjunction with other anti-tumour therapeutic agents, for example in combination with topoisomerase inhibitors (e.g., etoposide), mitosis inhibitors (e.g., vinblastine), compounds which interact with nucleic acids (e.g., cis-platin, cyclophosphamide, adriamycin), hormone antagonists (e.g., tamoxifen), inhibitors of metabolic processes (e.g., 5-FU etc.), cytokines (e.g., interferons), antibodies, etc. For treating respiratory tract diseases, these compounds may be used on their own or in conjunction with other therapeutic agents for the airways, such as substances with a secretolytic, broncholytic and/or antiinflammatory activity. For treating diseases in the region of the gastrointestinal tract, these compounds may also be administered on their own or in conjunction with substances having an effect on motility or secretion. These combinations may be administered either simultaneously or sequentially.

These compounds may be administered either on their own or in conjunction with other active substances by intravenous, subcutaneous, intramuscular, intraperitoneal or intranasal route, by inhalation or transdermally or orally, whilst aerosol formulations are particularly suitable for inhalation.

For pharmaceutical use the compounds according to the invention are generally used for warm-blooded vertebrates, particularly humans, in doses of 0.01–100 mg/kg of body weight, preferably 0.1–15 mg/kg. For administration they are formulated with one or more conventional inert carriers and/or diluents, e.g., with corn starch, lactose, glucose, microcrystalline cellulose, magnesium stearate, polyvinylpyrrolidone, citric acid, tartaric acid, water, water/ethanol, water/glycerol, water/sorbitol, water/polyethylene glycol, propylene glycol, stearyl alcohol, carboxymethylcellulose or fatty substances such as hard fat or suitable mixtures thereof in conventional galenic preparations such as plain or coated tablets, capsules, powders, suspensions, solutions, sprays or suppositories.

The following Examples are intended to illustrate the present invention without restricting it:

Preparation of the starting compounds:

EXAMPLE I

6-Amino-4-[(3-bromophenyl)amino]-7-[3-(1-methylpiperidin-4-yl)propyloxy]quinazoline 1.00 g of 4-[(3-bromophenyl)amino]-7-[3-(1-methylpiperidin-4-yl)propyloxy]-6-nitroquinazoline is dissolved in 16 ml of water, 35 ml of ethanol and 1.3 ml of glacial acetic acid and heated to boiling. Then 540 mg of iron powder are added with stirring. The reaction mixture is refluxed for about another 35 minutes. For working up the cooled reaction mixture is diluted with 15 ml of ethanol, made alkaline with 15 N sodium hydroxide solution, combined with 20 g of Extrelute and stirred for about 20 minutes. The precipitate formed is suction filtered and washed with 200 ml of warm ethanol. The filtrate is concentrated by evaporation, mixed with about 30 ml of water and extracted 3× with 70 ml of methylene chloride/methanol (9:1) each time. The combined extracts are dried over sodium sulfate and concentrated by evaporation, leaving a beige solid. Yield: 716 mg (76% of theory); melting point: 191° C.–198° C.; mass spectrum (ESI$^+$): m/z=470, 472 [M+H]$^+$.

The following compounds are obtained analogously to Example I:
(1) 6-Amino-4-[(3-bromophenyl)amino]-7-[2-(1-methylpiperidin-4-yl)ethoxy]quinazoline Melting point: 197° C.; mass spectrum (ESI$^+$): m/z=456, 458 [M+H]$^+$.
(2) 6-Amino-4-[(3-bromophenyl)amino]-7-[(1-methylpiperidin-4-yl)methoxy]quinazoline Melting point: 207° C.–208° C.; mass spectrum (ESI$^+$): m/z=442, 444 [M+H]$^+$.

(3) 6-Amino-4-[(3-bromophenyl)amino]-7-[(1-methylpiperidin-4-yl)oxy]quinazoline

Melting point: 170° C.; mass spectrum (ESI$^+$): m/z=428, 430 [M+H]$^+$.

(4) 6-Amino-4-[(3-chloro-4-fluorophenyl)amino]-7-cyclopropylmethoxyquinazoline

Melting point: 209° C.; $R_f$ value: 0.68 (silica gel, ethyl acetate).

(5) 6-Amino-4-[(3-chloro-4-fluorophenyl)amino]-7-cyclobutyloxyquinazoline $R_f$ value: 0.32 (silica gel, cyclohexane/ethyl acetate=3:4); mass spectrum (ESI$^+$): m/z=359, 361 [M+H]$^+$.

(6) 6-Amino-4-[(3-chloro-4-fluorophenyl)amino]-7-cyclopentyloxyquinazoline $R_f$ value: 0.33 (silica gel, cyclohexane/ethyl acetate=1:1); mass spectrum (ESI$^+$): m/z=373, 375 [M+H]$^+$.

(7) 6-Amino-4-[(R)-(1-phenylethyl)amino]-7-cyclobutyloxyquinazoline $R_f$ value: 0.28 (silica gel, ethyl acetate); mass spectrum (ESI$^+$): m/z=335 [M+H]$^+$.

(8) 6-Amino-4-[(R)-(1-phenylethyl)amino]-7-cyclopropylmethoxyquinazoline $R_f$ value: 0.54 (silica gel, ethyl acetate); mass spectrum (ESI$^+$): m/z=335 [M+H]$^+$.

(9) 6-Amino-4-[(R)-(1-phenylethyl)amino]-7-cyclopentyloxyquinazoline $R_f$ value: 0.20 (silica gel, ethyl acetate); mass spectrum (ESI$^+$): m/z=349 [M+H]$^+$.

(10) 6-Amino-4-[(3-chloro-4-fluorophenyl)amino]-7-[3-(1-methylpiperidin-4-yl)propyloxy]quinazoline $R_f$ value: 0.12 (silica gel, methylene chloride/methanol/concentrated aqueous ammonia solution=90:10:0.1); mass spectrum (ESI$^+$): m/z=444, 446 [M+H]$^+$.

(11) 6-Amino-4-[(3-chloro-4-fluorophenyl)amino]-7-[(tetrahydrofuran-2-yl)methoxy]quinazoline Melting point: 162° C.–164° C.; $R_f$ value: 0.55 (silica gel, ethyl acetate/methanol=9:1); mass spectrum (ESI$^-$): m/z=387, 389 [M–H]$^-$.

(12) 6-Amino-4-[(3-chloro-4-fluorophenyl)amino]-7-[(S)-(tetrahydrofuran-3-yl)oxy]quinazoline $R_f$ value: 0.27 (silica gel, ethyl acetate/methanol=9:1); mass spectrum (ESI$^-$): m/z=373, 375 [M–H]$^-$.

(13) 6-Amino-4-[(3-chloro-4-fluorophenyl)amino]-7-[(tetrahydropyran-4-yl)oxy]quinazoline $R_f$ value: 0.41 (silica gel, ethyl acetate/methanol=9:1); mass spectrum (ESI$^-$): m/z=387, 389 [M–H]$^-$.

(14) 6-Amino-4-[(R)-(1-phenylethyl)amino]-7-[2-(azetidin-1-yl)-ethoxy]quinazoline $R_f$ value: 0.37 (silica gel, methylene chloride/methanol/concentrated aqueous ammonia solution=90:10:0.1); mass spectrum (ESI$^+$): m/z=364 [M+H]$^+$.

(15) 6-Amino-4-[(R)-(1-phenylethyl)amino]-7-[2-(4-methyl-perhydro-1,4-diazepin-1-yl)-ethoxy]quinazoline $R_f$ value: 0.10 (silica gel, methylene chloride/methanol/concentrated aqueous ammonia solution=90:10:1); mass spectrum (ESI$^+$): m/z=421 [M+H]$^+$.

(16) 6-Amino-4-[(3-chloro-4-fluorophenyl)amino]-7-[3-(4-methyl-perhydro-1,4-diazepin-1-yl)propyloxy]quinazoline $R_f$ value: 0.09 (silica gel, methylene chloride/methanol/concentrated aqueous ammonia solution=90:10:0.1); mass spectrum (ESI$^+$): m/z=459, 461 [M+H]$^+$.

(17) 6-Amino-4-[(3-chloro-4-fluorophenyl)amino]-7-[3-(azetidin-1-yl)propyloxy]quinazoline $R_f$ value: 0.11 (silica gel, methylene chloride/methanol/concentrated aqueous ammonia solution=90:10:0.1); mass spectrum (ESI$^+$): m/z=402, 404 [M+H]$^+$.

EXAMPLE II

4-[(3-Bromophenyl)amino]-7-[3-(1-methylpiperidin-4-yl)propyloxy]-6-nitroquinazoline To a solution of 1.45 g of 3-(1-methylpiperidin-4-yl)propan-1-ol in 40 ml of tetrahydrofuran are added 360 mg of sodium hydride. The white suspension formed is stirred for 15 minutes at 65° C., cooled and mixed with 1.45 g of 4-[(3-bromophenyl)amino]-7-fluoro-6-nitroquinazoline, whereupon the mixture suddenly turns dark red. The reaction mixture is stirred first for 10 minutes at ambient temperature, then for 45 minutes at 65° C. As the reaction is not yet complete, a further 150 mg of sodium hydride are added and the mixture is stirred for a further 45 minutes at 65° C. The solvent is distilled off using a rotary evaporator and the brown residue is stirred with 50 ml of ice water. The aqueous phase is extracted with methylene chloride. The combined extracts are washed with water, dried over sodium sulfate and concentrated by evaporation. The crude product is purified by chromatography over a silica gel column with methylene chloride/methanol/concentrated ammonia solution (90:10:0.05). Yield: 1.30 g of (65% of theory); $R_f$ value: 0.28 (silica gel, methylene chloride/methanol/concentrated aqueous ammonia solution=90:10:0.1); mass spectrum (ESI$^+$): m/z=500, 502 [M+H]$^+$.

The following compounds are prepared analogously to Example II:

(1) 4-[(3-Bromophenyl)amino]-7-[2-(1-methylpiperidin-4-yl)ethoxy]-6-nitroquinazoline Melting point: 152° C.; mass spectrum (ESI$^+$): m/z=486, 488 [M+H]$^+$.

(2) 4-[(3-Bromophenyl)amino]-7-[(1-methylpiperidin-4-yl)methoxy]-6-nitroquinazoline Melting point: 205° C.–207° C.; mass spectrum (ESI$^+$): m/z=472, 474 [M+H]$^+$.

(3) 4-[(3-Bromophenyl)amino]-7-[(1-methylpiperidin-4-yl)oxy]-6-nitroquinazoline

Melting point: 219° C.; mass spectrum (ESI$^+$): m/z=458, 460 [M+H]$^+$.

(4) 4-[(3-Chloro-4-fluorophenyl)amino]-7-cyclopropylmethoxy-6-nitroquinazoline

Carried out in dimethylformamide with potassium tert-butoxide as base. Melting point: 211° C.–213° C.; mass spectrum (ESI$^+$): m/z=389, 391 [M+H]$^+$.

(5) 4-[(3-Chloro-4-fluorophenyl)amino]-7-cyclobutyloxy-6-nitroquinazoline

Carried out in dimethylformamide with potassium tert-butoxide as base. Melting point: 235° C.; $R_f$ value: 0.65 (silica gel, cyclohexane/ethyl acetate=3:4).

(6) 4-[(3-Chloro-4-fluorophenyl)amino]-7-cyclopentyloxy-6-nitroquinazoline

Carried out in dimethylformamide with potassium tert-butoxide as base. Melting point: 230° C.; mass spectrum (ESI$^+$): m/z=403, 405 [M+H]$^+$.

(7) 4-[(R)-(1-Phenylethyl)amino]-7-cyclobutyloxy-6-nitroquinazoline

Carried out in dimethylformamide with potassium tert-butoxide as base. Melting point: 108° C.–110° C.; $R_f$ value: 0.54 (silica gel, ethyl acetate).

(8) 4-[(R)-(1-Phenylethyl)amino]-7-cyclopropylmethoxy-6-nitroquinazoline

Carried out in dimethylformamide with potassium tert-butoxide as base. Melting point: 155° C.; $R_f$ value: 0.24 (silica gel, cyclohexane/ethyl acetate=1:1).
(9) 4-[(R)-(1-Phenylethyl)amino]-7-cyclopentyloxy-6-nitroquinazoline Carried out in dimethylformamide with potassium tert-butoxide as base. $R_f$ value: 0.24 (silica gel, petroleum ether/ethyl acetate=1:1); mass spectrum (ESI$^+$): m/z=379 [M+H]$^+$.
(10) 4-[(3-Chloro-4-fluorophenyl)amino]-6-nitro-7-[3-(1-methylpiperidin-4-yl)propyloxy]quinazoline $R_f$ value: 0.30 (silica gel, methylene chloride/methanol/concentrated aqueous ammonia solution=90:10:0.1); mass spectrum (ESI$^-$): m/z=474, 476 [M+H]$^+$.
(11) 4-[(3-Chloro-4-fluorophenyl)amino]-7-[(tetrahydrofuran-2-yl)methoxy]-6-nitroquinazoline Carried out in dimethylformamide with potassium tert-butoxide as base. $R_f$ value: 0.47 (silica gel, ethyl acetate); mass spectrum (ESI$^-$): m/z=417, 419 [M−H]$^-$.
(12) 4-[(3-Chloro-4-fluorophenyl)amino]-7-[(S)-(tetrahydrofuran-3-yl)oxy]-6-nitroquinazoline Carried out in dimethylformamide with potassium tert-butoxide as base. $R_f$ value: 0.45 (silica gel, ethyl acetate); mass spectrum (ESI$^-$): m/z=403, 405 [M−H]$^-$.
(13) 4-[(3-Chloro-4-fluorophenyl)amino]-7-[(tetrahydropyran-4-yl)oxy]-6-nitroquinazoline Carried out in dimethylformamide with potassium tert-butoxide as base. $R_f$ value: 0.41 (silica gel, ethyl acetate); mass spectrum (ESI$^-$): m/z=417, 419 [M−H]$^-$.
(14) 4-[(R)-(1-Phenylethyl)amino]-7-[2-(tetrahydropyran-2-yloxy)ethoxy]-6-nitroquinazoline $R_f$ value: 0.12 (silica gel, cyclohexane/ethyl acetate=1:1); mass spectrum (ESI$^+$): m/z=439 [M+H].
(15) 4-[(3-Chloro-4-fluorophenyl)amino]-7-{3-[(tert-butyldimethylsilyl)oxy]propyloxy}-6-nitroquinazoline (carried out in dimethylformamide with potassium tert-butoxide as base)

$R_f$ value: 0.87 silica gel, methylene chloride/methanol/concentrated aqueous ammonia solution=90:10:0.1); mass spectrum (ESI$^+$): m/z=507, 509 [M+H]$^+$.

EXAMPLE III

4-[(R)-(1-Phenylethyl)amino]-6-nitro-7-fluoro-quinazoline

A solution of 74 ml of (R)-1-phenylethylamine in 100 ml of dioxane is dropped into 108.8 g of 4-chloro-6-nitro-7-fluoro-quinazoline in 800 ml of methylene chloride with cooling. The reaction mixture is washed with water after stirring overnight at room temperature, the organic phase is separated, dried and evaporated. The obtained residue is purified by chromatography over a silica gel column (petroleum ether/ethyl acetate=1:1). Yield: 52.9 g (35% of theory); melting point: 203° C.; mass spectrum (ESI$^+$): m/z=313 [M+H]$^+$.

EXAMPLE IV

4-[(R)-(1-Phenylethyl)amino]-7-[2-(azetidin-1-yl)ethoxy]-6-nitroquinazoline 221 mg of dried potassium carbonate and 50 mg of sodium iodide were given to 600 mg of 4-[(R)-(1-phenylethyl)amino]-7-[2-methanesulfonyloxyethoxy]-6-nitroquinazoline and 0.34 ml of azetidine in 5.0 ml of acetonitrile. The reaction mixture was heated up to 70° C. with stirring. Subsequently 3 ml of acetonitrile were added after one hour and the mixture was stirred for further about 40 hours at 70° C. The solvent was removed in vacuo and the obtained residue was mixed with ice water. The precipitate was suction filtered and dried. The aqueous phase was extracted with methylene chloride and evaporated. The combined precipitates were dissolved in ethyl acetate and stirred together with a little of silica gel and 120 mg of charcoal for further purification. The obtained suspension was filtered and evaporated yielding a yellow resin. Yield: 518 mg (95% of theory); $R_f$ value: 0.40 (silica gel, methylene chloride/methanol/concentrated aqueous ammonia solution 90:10:0.1); mass spectrum (ESI$^+$): m/z=394 [M+H]$^+$.

The following compounds were obtained analogously to Example IV:

(1) 4-[(R)-(1-Phenylethyl)amino]-7-[2-(4-methyl-perhydro-1,4-diazepin-1-yl)-ethoxy]-6-nitroquinazoline $R_f$ value: 0.30 (silica gel, methylene chloride/methanol/concentrated aqueous ammonia solution=90:10:0.1); mass spectrum (ESI$^+$): m/z=451 [M+H]$^+$.
(2) 4-[(3-Chloro-4-fluorophenyl)amino]-7-[3-(4-methyl-perhydro-1,4-diazepin-1-yl) propyloxy]-6-nitroquinazoline $R_f$ value: 0.34 (silica gel, methylene chloride/methanol/concentrated aqueous ammonia solution=80:20:0.1); mass spectrum (ESI$^+$): m/z=489, 491 [M+H]$^+$.
(3) 4-[(3-Chloro-4-fluorophenyl)amino]-7-[3-(azetidin-1-yl)propyloxy]-6-nitroquinazoline $R_f$ value: 0.23 silica gel, methylene chloride/methanol/concentrated aqueous ammonia solution=90:10:0.1); mass spectrum (ESI$^+$): m/z=432, 434 [M+H]$^+$.

EXAMPLE V

4-[(R)-(1-Phenylethyl)amino]-7-[2-(methanesulfonyloxy)ethoxy]-6-nitroquinazoline A solution of 1.79 ml methanesulfonic acid chloride in 10 ml of methylene chloride was dropped into a mixture of 8.08 g of 4-[(R)-(1-phenylethyl)amino]-7-(2-hydroxyethoxy)-6-nitroquinazoline and 4.53 ml of ethyl-diisopropylamine in 90 ml of methylene chloride with ice cooling. The reaction mixture was stirred about one hour at room temperature whereby further 0.4 ml of methanesulfonic acid chloride and 0.5 ml of ethyldiisopropylamine were added to complete the reaction. Subsequently the reaction mixture was mixed with ice water and stirred after addition of saturated aqueous sodium carbonate solution. The organic phase was separated, washed with water, dried over magnesium sulfate and evaporated. The obtained dark resinous residue was crystallized by stirring with little tert-butyl methyl ether, suction filtered and dried in an exsiccator. Yield: 9.72 g (99% of theory); melting point: 128° C.–134° C.; mass spectrum (ESI$^-$): m/z=431 [M−H]$^-$.

The following compound was obtained analogously to Example V:

(1) 4-[(3-Chloro-4-fluorophenyl)amino]-7-[3-(methanesulfonyloxy)propyloxy]-6-nitroquinazoline $R_f$ value: 0.75 (silica gel, methylene chloride/methanol/concentrated aqueous ammonia solution=90:10:0.1); mass spectrum (ESI$^+$): m/z=471, 473 [M+H]$^+$.

EXAMPLE VI

4-[(R)-(1-Phenylethyl)amino]-7-(2-hydroxyethoxy)-6-nitroquinazoline 120 ml of methanol and 2 ml of concentrated hydrochloric acid were given to 8.05 g of 4-[(R)-(1-Phenylethyl) amino]-7-[2-(tetrahydropyran-2-yloxy)ethoxy]-6-nitroquinazoline. After stirring for 1.5 hours at 50° C. the reaction mixture was neutralized with concentrated aqueous sodium carbonate solution and evaporated. The solid residue was dissolved in ethyl acetate and the obtained solution was washed with water, with concentrated aqueous sodium chloride solution, dried over magnesium sulfate solution and evaporated. The obtained yellow residue was stirred with 20 ml of tert-butyl methyl ether, suction filtered and dried in an exsiccator. Yield: 4.53 g (91% of theory); melting point: 192° C.–194° C.; mass spectrum (ESI$^-$): m/z=353 [M–H]$^-$.

EXAMPLE VII

4-[(3-Chloro-4-fluorophenyl)amino]-7-(3-hydroxypropyloxy-6-nitroquinazoline

Prepared from 4-[(3-Chloro-4-fluorophenyl)amino]-7-{3-[(tert-butyl-dimethylsilyl)oxy]propyloxy}-6-nitroquinazoline by splitting off the protective silyl group with tetrabutyl ammonium fluoride in tetrahydrofuran. Yield: 94% of theory; R$_f$ value: 0.61 (silica gel, methylene chloride/methanol/concentrated aqueous ammonia solution=90:10:0.1); mass spectrum (ESI$^-$): m/z=391, 393 [M–H]$^-$.

Preparation of the end products:

EXAMPLE 1

4-[(3-Bromophenyl)amino]-7-[3-(1-methylpiperidin-4-yl)propyloxy]-6-[(vinylcarbonyl)amino]quinazoline To a solution of 300 mg of 6-amino-4-[(3-bromophenyl)amino]-7-[3-(1-methylpiperidin-4-yl)propyloxy]quinazoline in 7 ml of dichloromethane are added 0.28 ml of triethylamine. The reaction mixture is cooled to about –10° C. in an ice/sodium chloride cooling bath. Then a solution of 59 µl of acrylic acid chloride in 1 ml of tetrahydrofuran is added dropwise within 10 minutes. The cooling bath is removed and the mixture is stirred for a further 15 minutes at ambient temperature. For working up, the reaction mixture is poured on to 20 ml of ice water and mixed with 2–3 ml of 2 N sodium hydroxide solution, whereupon a light-colored precipitate is formed. The precipitate is suction filtered, washed with cold water and dissolved in dichloromethane. The solution is dried over sodium sulfate and concentrated by evaporation. The resin-like crude product is purified by chromatography over a silica gel column with methylene chloride/methanol/concentrated ammonia solution (90:10:0.5). Yield: 118 mg (35% of theory); R$_f$ value: 0.35 (silica gel, methylene chloride/methanol/concentrated aqueous ammonia solution=90:10:0.1); mass spectrum (ESI$^+$): m/z=524, 526 [M+H]$^+$.

The following compounds are obtained analogously to Example 1:

(1) 4-[(3-Bromophenyl)amino]-7-[2-(1-methylpiperidin-4-yl)ethoxy]-6-[(vinylcarbonyl)amino]quinazoline Melting point: 129° C.; mass spectrum (ESI$^+$): m/z=510, 512 [M+H]$^+$.

(2) 4-[(3-Bromophenyl)amino]-7-[(1-methylpiperidin-4-yl)methoxy]-6-[(vinylcarbonyl)amino]quinazoline Melting point: 174° C.; mass spectrum (ESI$^+$): m/z=496, 498 [M+H]$^+$.

(3) 4-[(3-Bromophenyl)amino]-7-[(1-methylpiperidin-4-yl)oxy]-6-[(vinylcarbonyl)amino]quinazoline Melting point: 166° C.; mass spectrum (ESI$^+$): m/z=482, 484 [M+H]$^+$.

(4) 4-[(3-Bromophenyl)amino]-7-[(1-methylpiperidin-4-yl)oxy]-6-[(1-oxo-2-buten-1-yl)amino]quinazoline R$_f$ value: 0.67 (silica gel, methylene chloride/methanol/concentrated aqueous ammonia solution=40:10:0.5); mass spectrum (ESI$^+$): m/z=496, 498 [M+H]$^+$.

(5) 4-[(3-Bromophenyl)amino]-7-[(1-methylpiperidin-4-yl)methoxy]-6-[(1-oxo-2-buten-1-yl)amino]quinazoline R$_f$ value: 0.45 (aluminium oxide, activity III; ethyl acetate/methanol=4:1); mass spectrum (EI): m/z=509, 511 [M]$^+$.

(6) 4-[(3-Bromophenyl)amino]-7-[3-(1-methylpiperidin-4-yl)propyloxy]-6-[(3-ethoxycarbonyl-1-oxo-2-propen-1-yl)amino]quinazoline R$_f$ value: 0.28 (silica gel, methylene chloride/methanol/concentrated aqueous ammonia solution=90:10:0.1); mass spectrum (ESI$^+$): m/z=596, 598 [M+H]$^+$.

(7) 4-[(3-Chloro-4-fluorophenyl)amino]-7-[3-(1-methylpiperidin-4-yl)propyloxy]-6-[(vinylcarbonyl)amino]quinazoline R$_f$ value: 0.33 (silica gel, methylene chloride/methanol/concentrated aqueous ammonia solution=90:10:0.1); mass spectrum (ESI$^+$): m/z=498, 500 [M+H]$^+$.

(8) 4-[(R)-(1-Phenylethyl)amino]-7-[2-(azetidin-1-yl)-ethoxy]-6-[(vinylcarbonyl)amino]quinazoline R$_f$ value: 0.60 (silica gel, methylene chloride/methanol/concentrated aqueous ammonia solution=90:10:0.1); mass spectrum (ESI$^-$): m/z=416 [M–H]$^-$.

(9) 4-[(R)-(1-Phenylethyl)amino]-7-[2-(4-methyl-perhydro-1,4-diazepin-1-yl)-ethoxy]-6-[(vinylcarbonyl)amino]quinazoline R$_f$ value: 0.37 (silica gel, methylene chloride/methanol/concentrated aqueous ammonia solution=90:10:0.1); mass spectrum (ESI$^-$): m/z=473 [M–H]$^-$.

(10) 4-[(3-Chloro-4-fluorophenyl)amino]-7-[3-(4-methyl-perhydro-1,4-diazepin-1-yl)propyloxy]-6-[(vinylcarbonyl)amino]quinazoline R$_f$ value: 0.29 (silica gel, methylene chloride/methanol/concentrated aqueous ammonia solution=90:10:0.1); mass spectrum (ESI$^+$): m/z=513, 515 [M+H]$^+$.

(11) 4-[(3-Chloro-4-fluorophenyl)amino]-7-[3-(azetidin-1-yl)propyloxy]-6-[(vinylcarbonyl)amino]quinazoline R$_f$ value: 0.39 (silica gel, methylene chloride/methanol/concentrated aqueous ammonia solution=90:10:0.1); mass spectrum (ESI$^-$): m/z=454, 456 [M–H]$^-$.

EXAMPLE 2

4-[(3-Bromophenyl)amino]-7-[3-(1-methylpiperidin-4-yl)propyloxy]-6-[(1-oxo-2,4-hexadien-1-yl)amino]quinazoline To 31 mg of sorbic acid in 1 ml of tetrahydrofuran are added 40 µl of isobutyl chloroformate followed by 45 µl of N-methylmorpholine whilst cooling with an ice bath. The white suspension is stirred for one minute, then a solution of 100 mg of 6-amino-4-[(3-bromophenyl)amino]-7-[3-(1-methylpiperidin-4-yl)propyloxy]quinazoline in 1.5 ml of pyridine is added. The ice bath is removed and the reaction mixture is stirred overnight. For working up, it is poured onto 20 ml of ice water, stirred for 30 minutes and adjusted to pH 9–10 with a few drops of 2 N sodium hydroxide solution. The aqueous phase is extracted with methylene chloride, the combined organic phases are dried over sodium sulfate and concentrated by evaporation. The resin-like crude product is purified by chromatography over an aluminium oxide column (activity III) with methylene chloride/methanol (99.5:0.5). Yield: 62 mg (52% of theory); $R_f$ value: 0.29 (aluminium oxide, activity III; methylene chloride/methanol=98:2); mass spectrum (EI): m/z=563, 565 [M]⁺.

The following compounds are obtained analogously to Example 2:
(1) 4-[(3-Bromophenyl)amino]-7-[3-(1-methylpiperidin-4-yl)propyloxy]-6-[(1-oxo-2-buten-1-yl)amino]quinazoline
$R_f$ value: 0.26 (aluminium oxide, activity III; methylene chloride/methanol=98:2); mass spectrum (ESI⁺): m/z=538, 540 [M+H]⁺.
(2) 4-[(3-Bromophenyl)amino]-7-[3-(1-methylpiperidin-4-yl)propyloxy]-6-[(3-phenyl-1-oxo-2-propen-1-yl)amino]quinazoline
$R_f$ value: 0.26 (aluminium oxide, activity III; methylene chloride/methanol=98:2); mass spectrum (EI): m/z=599, 601 [M]⁺.
(3) 4-[(3-Bromophenyl)amino]-7-[3-(1-methylpiperidin-4-yl)propyloxy]-6-[(1-oxo-2-butyn-1-yl)amino]quinazoline
$R_f$ value: 0.40 (aluminium oxide, activity III; methylene chloride/methanol=98:2); mass spectrum (ESI⁺): m/z=536, 538 [M+H]⁺.

EXAMPLE 3

4-[(3-Chloro-4-fluorophenyl)amino]-6-{[4-(N,N-diethylamino)-1-oxo-2-buten-1-yl]amino}-7-cyclopropylmethoxyquinazoline To a solution of 640 mg of 4-bromo-2-butenoic acid in 10 ml of methylene chloride are added, at ambient temperature, 0.67 ml of oxalyl chloride and one drop of dimethylformamide. The reaction mixture is stirred for about another half hour at ambient temperature, until the development of gas has ceased. The acid chloride formed is substantially freed from solvent in vacuo using a rotary evaporator. Then the crude product is dissolved in 10 ml of methylene chloride and added dropwise, whilst cooling with an ice bath, to a mixture of 1.00 g of 6-amino-4-[(3-chloro-4-fluorophenyl)amino]-7-cyclopropylmethoxyquinazoline and 1.60 ml of Hünig base in 50 ml of tetrahydrofuran. The reaction mixture is stirred for 1.5 hours in an ice bath and for a further 2 hours at ambient temperature. Then 2.90 ml of diethylamine are added and the mixture is stirred for 2.5 days at ambient temperature. To work it up, the reaction mixture is filtered and the filtrate is concentrated by evaporation. The filter residue is purified by chromatography over a silica gel column with ethyl acetate/methanol (19:1). Yield: 550 mg (40% of theory); melting point: 114° C.; mass spectrum (ESI⁺): m/z=498, 500 [M+H]⁺.

The following compounds are obtained analogously to Example 3:
(1) 4-[(3-Chloro-4-fluorophenyl)amino]-6-{[4-(morpholin-4-yl)-1-oxo-2-buten-1-yl]amino}-7-cyclopropylmethoxyquinazoline
$R_f$ value: 0.53 (silica gel, ethyl acetate/methanol=9:1); mass spectrum (ESI⁻): m/z=510, 512 [M−H]⁻.
(2) 4-[(3-Chloro-4-fluorophenyl)amino]-6-{[4-(4-ethylpiperazin-1-yl)-1-oxo-2-buten-1-yl]amino}-7-cyclopropylmethoxyquinazoline
$R_f$ value: 0.44 (silica gel, ethyl acetate/methanol/concentrated aqueous ammonia solution=9:1:0.1); mass spectrum (EI): m/z=538, 540 [M]⁺.
(3) 4-[(3-Chloro-4-fluorophenyl)amino]-6-{[4-(2,6-dimethyl-morpholin-4-yl)-1-oxo-2-buten-1-yl]amino}-7-cyclopropylmethoxyquinazoline
Melting point: 160° C.; mass spectrum (ESI⁺): m/z=540, 542 [M+H]⁺.
(4) 4-[(3-Chloro-4-fluorophenyl)amino]-6-{[4-(dimethylamino)-1-oxo-2-buten-1-yl]amino}-7-cyclopropylmethoxyquinazoline
Melting point: 137° C.; mass spectrum (ESI⁺): m/z=470, 472 [M+H]⁺.
(5) 4-[(3-Chloro-4-fluorophenyl)amino]-6-{[4-(1-oxidothiomorpholin-4-yl)-1-oxo-2-buten-1-yl]amino}-7-cyclopropylmethoxyquinazoline
Melting point: 239° C.; mass spectrum (ESI⁺): m/z=544, 546 [M+H]⁺.
(6) 4-[(3-Chloro-4-fluorophenyl)amino]-6-{[4-(morpholin-4-yl)-1-oxo-2-buten-1-yl]amino}-7-cyclobutyloxyquinazoline
$R_f$ value: 0.45 (silica gel, ethyl acetate/methanol=9:1); mass spectrum (ESI⁺): m/z=512, 514 [M+H]⁺.
(7) 4-[(3-Chloro-4-fluorophenyl)amino]-6-{[4-(morpholin-4-yl)-1-oxo-2-buten-1-yl]amino}-7-cyclopentyloxyquinazoline
Melting point: 143° C.; $R_f$ value: 0.45 (silica gel, ethyl acetate/methanol=9:1).
(8) 4-[(3-Chloro-4-fluorophenyl)amino]-6-{[4-(diethylamino)-1-oxo-2-buten-1-yl]amino}-7-cyclobutyloxyquinazoline
Melting point: 111° C.; $R_f$ value: 0.21 (silica gel, ethyl acetate/methanol=9:1).
(9) 4-[(3-Chloro-4-fluorophenyl)amino]-6-{[4-(diethylamino)-1-oxo-2-buten-1-yl]amino}-7-cyclopentyloxyquinazoline
Melting point: 105° C.; $R_f$ value: 0.23 (silica gel, ethyl acetate/methanol=9:1).
(10) 4-[(R)-(1-Phenylethyl)amino]-6-{[4-(morpholin-4-yl)-1-oxo-2-buten-1-yl]amino}-7-cyclobutyloxyquinazoline
$R_f$ value: 0.33 (silica gel, ethyl acetate/methanol=9:1); mass spectrum (ESI⁺): m/z=488 [M+H]⁺.
(11) 4-[(R)-(1-Phenylethyl)amino]-6-{[4-(morpholin-4-yl)-1-oxo-2-buten-1-yl]amino}-7-cyclopropylmethoxyquinazoline
$R_f$ value: 0.37 (silica gel, ethyl acetate/methanol=9:1); mass spectrum (ESI⁺): m/z=488 [M+H]⁺.
(12) 4-[(R)-(1-Phenylethyl)amino]-6-{[4-(morpholin-4-yl)-1-oxo-2-buten-1-yl]amino}-7-cyclopentyloxyquinazoline
$R_f$ value: 0.35 (silica gel, ethyl acetate/methanol=9:1); mass spectrum (ESI⁺): m/z=502 [M+H]⁺.
(13) 4-[(R)-(1-Phenylethyl)amino]-6-{[4-(diethylamino)-1-oxo-2-buten-1-yl]amino}-7-cyclobutyloxyquinazoline
$R_f$ value: 0.26 (silica gel, ethyl acetate/methanol=4:1); mass spectrum (ESI⁺): m/z=474 [M+H]⁺.
(14) 4-[(R)-(1-Phenylethyl)amino]-6-{[4-(diethylamino)-1-oxo-2-buten-1-yl]amino}-7-cyclopentyloxyquinazoline
$R_f$ value: 0.31 (silica gel, ethyl acetate/methanol=4:1); mass spectrum (ESI⁺): m/z=488 [M+H]⁺.
(15) 4-[(R)-(1-Phenylethyl)amino]-6-{[4-(diethylamino)-1-oxo-2-buten-1-yl]amino}-7-cyclopropylmethoxyquinazoline
$R_f$ value: 0.15 (silica gel, ethyl acetate/methanol=9:1); mass spectrum (ESI⁺): m/z=474 [M+H]⁺.
(16) 4-[(3-Chloro-4-fluorophenyl)amino]-6-({4-[N-methyl-N-(1-methylpiperidin-4-yl)amino]-1-oxo-2-buten-1-yl}amino)-7-cyclopropylmethoxyquinazoline $R_f$ value: 0.28 (silica gel, ethyl acetate/methanol/concentrated aqueous ammonia solution=80:20:2); mass spectrum (ESI$^+$): m/z=553, 555 [M+H]$^+$.

(17) 4-[(3-Chloro-4-fluorophenyl)amino]-6-({4-[(R)-2-methoxymethylpyrrolidin-1-yl]-1-oxo-2-buten-1-yl}amino)-7-cyclopropylmethoxyquinazoline $R_f$ value: 0.33 (silica gel, ethyl acetate/methanol=9:1); mass spectrum (ESI$^+$): m/z=540, 542 [M+H]$^+$.

(18) 4-[(3-Chloro-4-fluorophenyl)amino]-6-({4-[(S)-2-methoxymethylpyrrolidin-1-yl]-1-oxo-2-buten-1-yl}amino)-7-cyclopropylmethoxyquinazoline Melting point: 120° C.; mass spectrum (ESI$^+$): m/z=540, 542 [M+H]$^+$.

(19) 4-[(3-Chloro-4-fluorophenyl)amino]-6-({4-[bis-(2-methoxyethyl)amino]-1-oxo-2-buten-1-yl}amino)-7-cyclopropylmethoxyquinazoline $R_f$ value: 0.51 (silica gel, ethyl acetate/methanol=9:1); mass spectrum (ESI$^+$): m/z=558, 560 [M+H]$^+$.

(20) 4-[(3-Chloro-4-fluorophenyl)amino]-6-({4-[N-ethyl-N-(2-methoxyethyl)amino]-1-oxo-2-buten-1-yl}amino)-7-cyclopropylmethoxyquinazoline $R_f$ value: 0.33 (silica gel, ethyl acetate/methanol=9:1); mass spectrum (ESI$^+$): m/z=528, 530 [M+H]$^+$.

(21) 4-[(3-Chloro-4-fluorophenyl)amino]-6-{[4-(piperidin-1-yl)-1-oxo-2-buten-1-yl]amino}-7-cyclopropylmethoxyquinazoline $R_f$ value: 0.22 (silica gel, ethyl acetate/methanol=9:1); mass spectrum (ESI$^+$): m/z=510, 512 [M+H]$^+$.

(22) 4-[(3-Chloro-4-fluorophenyl)amino]-6-{[4-(2-methylpiperidin-1-yl)-1-oxo-2-buten-1-yl]amino}-7-cyclopropylmethoxyquinazoline $R_f$ value: 0.21 (silica gel, ethyl acetate/methanol=9:1); mass spectrum (ESI$^+$): m/z=524, 526 [M+H]$^+$.

(23) 4-[(3-Chloro-4-fluorophenyl)amino]-6-{[4-(pyrrolidin-1-yl)-1-oxo-2-buten-1-yl]amino}-7-cyclopropylmethoxyquinazoline $R_f$ value: 0.10 (silica gel, ethyl acetate/methanol=9:1); mass spectrum (ESI$^+$): m/z=496, 498 [M+H]$^+$.

(24) 4-[(3-Chloro-4-fluorophenyl)amino]-6-{[4-(4-cyclopropylmethylpiperazin-1-yl)-1-oxo-2-buten-1-yl]amino}-7-cyclopropylmethoxyquinazoline Melting point: 117° C.; mass spectrum (ESI$^+$): m/z=565, 567 [M+H]$^+$.

(25) 4-[(3-Chloro-4-fluorophenyl)amino]-6-{[4-(2-methylpyrrolidin-1-yl)-1-oxo-2-buten-1-yl]amino}-7-cyclopropylmethoxyquinazoline Melting point: 108° C.–110° C.; $R_f$ value: 0.27 (silica gel, ethyl acetate/methanol=9:1).

(26) 4-[(3-Chloro-4-fluorophenyl)amino]-6-({4-[N-methyl-N-(tetrahydropyran-4-yl)amino]-1-oxo-2-buten-1-yl}amino)-7-cyclopropylmethoxyquinazoline $R_f$ value: 0.29 (silica gel, ethyl acetate/methanol=9:1); mass spectrum (ESI$^-$): m/z=538, 540 [M–H]$^-$.

(27) 4-[(3-Chloro-4-fluorophenyl)amino]-6-{[4-(cis-2,6-dimethylpiperidin-1-yl)-1-oxo-2-buten-1-yl]amino}-7-cyclopropylmethoxyquinazoline $R_f$ value: 0.27 (silica gel, ethyl acetate/methanol=9:1); mass spectrum (ESI$^-$): m/z=536, 538 [M–H]$^-$.

(28) 4-[(3-Chloro-4-fluorophenyl)amino]-6-{[4-(2,5-dimethylpyrrolidin-1-yl)-1-oxo-2-buten-1-yl]amino}-7-cyclopropylmethoxyquinazoline $R_f$ value: 0.36 (silica gel, ethyl acetate/methanol=9:1); mass spectrum (ESI$^-$): m/z=522, 524 [M–H]$^+$.

(29) 4-[(3-Chloro-4-fluorophenyl)amino]-6-({4-[(diethylamino)-1-oxo-2-buten-1-yl]amino}-7-[(tetrahydrofuran-2-yl)methoxy]quinazoline $R_f$ value: 0.35 (silica gel, ethyl acetate/methanol/concentrated aqueous ammonia solution=9:1:0.1); mass spectrum (ESI$^-$): m/z 526, 528 [M–H]$^-$.

(30) 4-[(3-Chloro-4-fluorophenyl)amino]-6-{[4-(diethylamino)-1-oxo-2-buten-1-yl]amino}-7-[(S)-(tetrahydrofaran-3-yl)oxy]quinazoline Melting point: 119° C.; mass spectrum (ESI$^-$): m/z=512, 514 [M–H]$^-$.

(31) 4-[(3-Chloro-4-fluorophenyl)amino]-6-{[4-(4-diethylaminomethylpiperidin-1-yl)-1-oxo-2-buten-1-yl]amino}-7-cyclopropylmethoxyquinazoline $R_f$ value: 0.20 (silica gel, methylene chloride/methanol=9:1); mass spectrum (ESI$^-$): m/z=593, 595 [M–H]$^-$.

(32) 4-[(3-Chloro-4-fluorophenyl)amino]-6-{[4-(N-methyl-N-cyclopropylmethyl-amino)-1-oxo-2-buten-1-yl]amino}-7-cyclopropylmethoxyquinazoline $R_f$ value: 0.73 (silica gel, methylene chloride/methanol=9:1); mass spectrum (ESI$^+$): m/z=510, 512 [M+H]$^+$.

(33) 4-[(3-Chloro-4-fluorophenyl)amino]-6-({4-[N-methyl-N-(2-methoxypropyl)amino]-1-oxo-2-buten-1-yl}amino)-7-cyclopropylmethoxyquinazoline The N-methyl-N-(2-methoxypropyl)amine used was prepared by reaction of 2-methoxypropionic acid chloride with methylamine and subsequent reduction with lithium aluminium hydride; melting point: 123° C.–125° C.; $R_f$ value: 0.66 (silica gel, methylene chloride/methanol=9:1).

(34) 4-[(3-Chloro-4-fluorophenyl)amino]-6-({4-[N-methyl-N-(3-methoxypropyl)amino]-1-oxo-2-buten-1-yl}amino)-7-cyclopropylmethoxyquinazoline $R_f$ value: 0.66 (silica gel, methylene chloride/methanol=9:1); mass spectrum (ESI$^+$): m/z=528, 530 [M+H]$^+$.

(35) 4-[(3-Chloro-4-fluorophenyl)amino]-6-{[4-(4-methoxypiperidin-1-yl)-1-oxo-2-buten-1-yl]amino}-7-cyclopropylmethoxyquinazoline Melting point: 129° C.–130° C.; $R_f$ value: 0.20 (silica gel, ethyl acetate/methanol=9:1); mass spectrum (ESI$^-$): m/z=538, 540 [M–H]$^-$.

(36) 4-[(3-Chloro-4-fluorophenyl)amino]-6-{[4-(4-hydroxypiperidin-1-yl)-1-oxo-2-buten-1-yl]amino}-7-cyclopropylmethoxyquinazoline $R_f$ value: 0.30 (silica gel, methylene chloride/methanol/concentrated aqueous ammonia solution=9:1:0.1); mass spectrum (ESI$^-$): m/z=524, 526 [M–H]$^-$.

(37) 4-[(3-Chloro-4-fluorophenyl)amino]-6-{[4-(diethylamino)-1-oxo-2-buten-1-yl]amino}-7-[(tetrahydropyran-4-yl)oxy]quinazoline $R_f$ value: 0.47 (silica gel, methylene chloride/methanol=9:1); mass spectrum (ESI$^-$): m/z=528, 530 [M–H]$^-$.

(38) 4-[(3-Chloro-4-fluorophenyl)amino]-6-({4-[N-methyl-N-(tetrahydrofuran-2-ylmethyl)amino]-1-oxo-2-buten-1-yl}amino)-7-cyclopropylmethoxyquinazoline Melting point: about 145° C. (decomp.); $R_f$ value: 0.23 (silica gel, methylene chloride/methanol=15:1); Mass spectrum (ESI$^+$): m/z=540, 542 [M+H]$^+$.

(39) 4-[(3-Chloro-4-fluorophenyl)amino]-6-({4-[N-methyl-N-(tetrahydrofuran-3-yl)amino]-1-oxo-2-buten-1-yl}amino)-7-cyclopropylmethoxyquinazoline The starting N-methyl-N-(3-tetrahydrofuranyl)amine was prepared by reaction of tetrahydrofaran-3-carboxylic acid with diphenyl phosphonate azide in benzyl alcohol and subsequent reduction of the obtained 3-(benzyloxycarbonylamino)tetrahydrofuran with lithium aluminium hydride. Melting point: 157° C.–159° C.; $R_f$ value: 0.23 (silica gel, methylene chloride/methanol=15:1); mass spectrum (ESI$^+$): m/z=526, 528 [M+H]$^+$.

(40) 4-[(3-Chloro-4-fluorophenyl)amino]-6-({4-[N-methyl-N-(1-methoxy-2-propyl)amino]-1-oxo-2-buten-1-yl}amino)-7-cyclopropylmethoxyquinazoline The starting N-methyl-N-(1-methoxy-2-propyl)amine was prepared by reductive amination of methoxyacetone with methylamine hydrochloride and sodium triacetoxyborohydride in the presence of sodium acetate. The reaction was carried out in tetrahydrofuran. $R_f$ value: 0.38 (silica gel, ethyl acetate/methanol=9:1); mass spectrum (ESI$^+$): m/z 528, 530 [M+H]$^+$.

The following compounds may also be obtained analogously to the above Examples and other methods known from the literature:

(1) 4-[(3-Chloro-4-fluorophenyl)amino]-6-{[4-(N,N-dimethylamino)-1-oxo-2-buten-1-yl]amino}-7-cyclopropylmethoxyquinazoline (2) 4-[(3-Chloro-4-fluorophenyl)amino]-6-{[4-(N,N-dibutylamino)-1-oxo-2-buten-1-yl]amino}-7-cyclopropylmethoxyquinazoline (3) 4-[(3-Chloro-4-fluorophenyl)amino]-6-{[4-(piperidin-1-yl)-1-oxo-2-buten-1-yl]amino}-7-cyclopropylmethoxyquinazoline (4) 4-[(3-Chloro-4-fluorophenyl)amino]-6-{[4-(2,6-dimethylmorpholin-4-yl)-1-oxo-2-buten-1-yl]amino}-7-cyclopropylmethoxyquinazoline (5) 4-[(3-Chloro-4-fluorophenyl)amino]-6-{[4-(4-methylpiperazin-1-yl)-1-oxo-2-buten-1-yl]amino}-7-cyclopropylmethoxyquinazoline (6) 4-[(3-Chloro-4-fluorophenyl)amino]-6-{[4-(4-cyclopropylmethylpiperazin-1-yl)-1-oxo-2-buten-1-yl]amino}-7-cyclopropylmethoxyquinazoline (7) 4-[(3-Chloro-4-fluorophenyl)amino]-6-{[4-(4-cyclopropylpiperazin-1-yl)-1-oxo-2-buten-1-yl]amino}-7-cyclopropylmethoxyquinazoline (8) 4-[(3-Chloro-4-fluorophenyl)amino]-6-{[4-(4-methylsulfonylpiperazin-1-yl)-1-oxo-2-buten-1-yl]amino}-7-cyclopropylmethoxyquinazoline (9) 4-[(3-Chloro-4-fluorophenyl)amino]-6-{[4-(4-acetylpiperazin-1-yl)-1-oxo-2-buten-1-yl]amino}-7-cyclopropylmethoxyquinazoline

(10) 4-[(3-Chloro-4-fluorophenyl)amino]-6-[(4-{4-[(N,N-di-methylamino)carbonyl]piperazin-1-yl}-1-oxo-2-buten-1-yl)amino]-7-cyclopropylmethoxyquinazoline

(11) 4-[(3-Chloro-4-fluorophenyl)amino]-6-{[4-(pyrrolidin-1-yl)-1-oxo-2-buten-1-yl]amino}-7-cyclopropylmethoxyquinazoline

(12) 4-[(3-Chloro-4-fluorophenyl)amino]-6-{[4-(N-cyclopropyl-N-methylamino)-1-oxo-2-buten-1-yl]amino}-7-cyclopropylmethoxyquinazoline

(13) 4-[(3-Chloro-4-fluorophenyl)amino]-6-{[4-(N-cyclopropylmethyl-N-methylamino)-1-oxo-2-buten-1-yl]amino}-7-cyclopropylmethoxyquinazoline

(14) 4-[(3-Chloro-4-fluorophenyl)amino]-6-{[4-(N,N-dimethylamino)-1-oxo-2-butyn-1-yl]amino}-7-cyclopropylmethoxyquinazoline

(15) 4-[(3-Chloro-4-fluorophenyl)amino]-6-{[4-(N,N-diethylamino)-1-oxo-2-butyn-1-yl]amino}-7-cyclopropylmethoxyquinazoline

(16) 4-[(3-Chloro-4-fluorophenyl)amino]-6-{[4-(piperidin-1-yl)-1-oxo-2-butyn-1-yl]amino}-7-cyclopropylmethoxyquinazoline

(17) 4-[(3-Chloro-4-fluorophenyl)amino]-6-{[4-(morpholin-4-yl)-1-oxo-2-butyn-1-yl]amino}-7-cyclopropylmethoxyquinazoline

(18) 4-[(3-Chloro-4-fluorophenyl)amino]-6-{[4-(4-methylpiperazin-1-yl)-1-oxo-2-butyn-1-yl]amino}-7-cyclopropylmethoxyquinazoline

(19) 4-[(3-Chloro-4-fluorophenyl)amino]-6-{[4-(4-methylsulfonylpiperazin-1-yl)-1-oxo-2-butyn-1-yl]amino}-7-cyclopropylmethoxyquinazoline

(20) 4-[(3-Chloro-4-fluorophenyl)amino]-6-{[4-(morpholin-4-yl)-1,4-dioxo-2-buten-1-yl]amino}-7-cyclopropylmethoxyquinazoline

(21) 4-[(3-Chloro-4-fluorophenyl)amino]-6-({4-[(3-N,N-dimethylamino-propan-1-yl)amino]-1,4-dioxo-2-buten-1-yl}amino)-7-cyclopropylmethoxyquinazoline

(22) 4-[(3-Chloro-4-fluorophenyl)amino]-6-({2-[(N,N-diethylamino)methyl]-1-oxo-2-propen-1-yl}amino)-7-cyclopropylmethoxyquinazoline

(23) 4-[(3-Chloro-4-fluorophenyl)amino]-6-{[4-(2-methoxymethylpyrrolidin-1-yl)-1-oxo-2-buten-1-yl]amino}-7-cyclopropylmethoxyquinazoline

(24) 4-[(3-Chloro-4-fluorophenyl)amino]-6-({4-[N,N-bis(2-methoxyethyl)amino]-1-oxo-2-buten-1-yl}amino)-7-cyclopropylmethoxyquinazoline

(25) 4-[(3-Chloro-4-fluorophenyl)amino]-6-({4-[N-(2-methoxyethyl)-N-methylamino]-1-oxo-2-buten-1-yl}amino)-7-cyclopropylmethoxyquinazoline

(26) 4-[(3-Chloro-4-fluorophenyl)amino]-6-{[4-(N,N-dimethylamino)-1-oxo-2-buten-1-yl]amino}-7-cyclobutylmethoxyquinazoline

(27) 4-[(3-Chloro-4-fluorophenyl)amino]-6-{[4-(N,N-dimethylamino)-1-oxo-2-buten-1-yl]amino}-7-cyclopentylmethoxyquinazoline

(28) 4-[(3-Chloro-4-fluorophenyl)amino]-6-{[4-(N,N-dimethylamino)-1-oxo-2-buten-1-yl]amino}-7-cyclohexylmethoxyquinazoline

(29) 4-[(3-Chloro-4-fluorophenyl)amino]-6-{[4-(N,N-dimethylamino)-1-oxo-2-buten-1-yl]amino}-7-(2-cyclopropyletoxy)quinazoline

(30) 4-[(3-Chloro-4-fluorophenyl)amino]-6-{[4-(N,N-dimethylamino)-1-oxo-2-buten-1-yl]amino}-7-(3-cyclopropylpropyloxy)quinazoline

(31) 4-[(3-Chloro-4-fluorophenyl)amino]-6-({4-[4-(tetrahydrofuran-3-yl)piperidin-1-yl]-1-oxo-2-buten-1-yl}amino)-7-cyclopropylmethoxyquinazoline

(32) 4-[(3-Chloro-4-fluorophenyl)amino]-6-({4-[4-(morpholin-4-yl)piperidin-1-yl]-1-oxo-2-buten-1-yl}amino)-7-cyclopropylmethoxyquinazoline

(33) 4-[(3-Chloro-4-fluorophenyl)amino]-6-({4-[4-(tetrahydrofuran-3-yl)piperazin-1-yl]-1-oxo-2-buten-1-yl}amino)-7-cyclopropylmethoxyquinazoline

(34) 4-[(3-Chloro-4-fluorophenyl)amino]-6-({4-[4-(tetrahydrofuran-2-ylmethyl)piperazin-1-yl]-1-oxo-2-buten-1-yl}amino)-7-cyclopropylmethoxyquinazoline

(35) 4-[(3-Chloro-4-fluorophenyl)amino]-6-[(4-{N-methyl-N-[1-(tetrahydrofuran-3-yl)piperidin-4-yl]amino}-1-oxo-2-buten-1-yl)amino]-7-cyclopropylmethoxyquinazoline

(36) 4-[(3-Chloro-4-fluorophenyl)amino]-6-({4-[(S)-2-methoxymethylpyrrolidin-1-yl]-1-oxo-2-buten-1-yl}amino)-7-cyclobutyloxyquinazoline

(37) 4-[(3-Chloro-4-fluorophenyl)amino]-6-({4-[(R)-2-methoxymethylpyrrolidin-1-yl]-1-oxo-2-buten-1-yl}amino)-7-cyclobutyloxyquinazoline

(38) 4-[(3-Chloro-4-fluorophenyl)amino]-6-({4-[bis-(2-methoxyethyl)amino]-1-oxo-2-buten-1-yl}amino)-7-cyclobutyloxyquinazoline

(39) 4-[(3-Chloro-4-fluorophenyl)amino]-6-({4-[N-methyl-N-(2-methoxyethyl)amino]-1-oxo-2-buten-1-yl}amino)-7-cyclobutyloxyquinazoline

(40) 4-[(3-Chloro-4-fluorophenyl)amino]-6-({4-[(S)-N-methyl-N-(1-methoxy-2-propyl)amino]-1-oxo-2-buten-1-yl}amino)-7-cyclobutyloxyquinazoline

(41) 4-[(3-Chloro-4-fluorophenyl)amino]-6-({4-[(R)-N-methyl-N-(1-methoxy-2-propyl)amino]-1-oxo-2-buten-1-yl}amino)-7-cyclobutyloxyquinazoline

(42) 4-[(3-Chloro-4-fluorophenyl)amino]-6-({4-[N-methyl-N-(1-methoxy-2-propyl)amino]-1-oxo-2-buten-1-yl}amino)-7-cyclopropylmethoxyquinazoline

(43) 4-[(3-Chloro-4-fluorophenyl)amino]-6-({4-[N-methyl-N-(2-methoxypropyl)amino]-1-oxo-2-buten-1-yl}amino)-7-cyclopropylmethoxyquinazoline

(44) 4-[(3-Chloro-4-fluorophenyl)amino]-6-({4-[N-methyl-N-(3-methoxypropyl)amino]-1-oxo-2-buten-1-yl}amino)-7-cyclopropylmethoxyquinazoline

(45) 4-[(3-Chloro-4-fluorophenyl)amino]-6-({4-[N-methyl-N-(tetrahydrofuran-3-yl)amino]-1-oxo-2-buten-1-yl}amino)-7-cyclopropylmethoxyquinazoline

(46) 4-[(3-Chloro-4-fluorophenyl)amino]-6-({4-[(S)-N-methyl-N-(tetrahydrofuran-3-yl)amino]-1-oxo-2-buten-1-yl}amino)-7-cyclobutyloxyquinazoline

(47) 4-[(3-Chloro-4-fluorophenyl)amino]-6-({4-[(R)-N-methyl-N-(tetrahydrofuran-3-yl)amino]-1-oxo-2-buten-1-yl}amino)-7-cyclobutyloxyquinazoline

(48) 4-[(3-Chloro-4-fluorophenyl)amino]-6-({4-[N-methyl-N-(tetrahydropyran-4-yl)amino]-1-oxo-2-buten-1-yl}amino)-7-cyclopropylmethoxyquinazoline

(49) 4-[(3-Chloro-4-fluorophenyl)amino]-6-({4-[N-methyl-N-(tetrahydropyran-4-yl)amino]-1-oxo-2-buten-1-yl}amino)-7-cyclobutyloxyquinazoline

(50) 4-[(3-Chloro-4-fluorophenyl)amino]-6-{[4-(4-cyclopropylpiperazin-1-yl)-1-oxo-2-buten-1-yl]amino}-7-cyclobutyloxyquinazoline

(51) 4-[(3-Chloro-4-fluorophenyl)amino]-6-{[4-(4-cyclopropylmethylpiperazin-1-yl)-1-oxo-2-buten-1-yl]amino}-7-cyclobutyloxyquinazoline

(52) 4-[(3-Chloro-4-fluorophenyl)amino]-6-{[4-(N-cyclopropyl-N-methylamino)-1-oxo-2-buten-1-yl]amino}-7-cyclobutyloxyquinazoline

(53) 4-[(3-Chloro-4-fluorophenyl)amino]-6-{[4-(N-cyclopropylmethyl-N-methyl-amino)-1-oxo-2-buten-1-yl]amino}-7-cyclobutyloxyquinazoline

(54) 4-[(3-Chloro-4-fluorophenyl)amino]-6-({4-[N-methyl-N-(tetrahydrofuran-2-ylmethyl)amino]-1-oxo-2-buten-1-yl}amino)-7-cyclopropylmethoxyquinazoline

(55) 4-[(3-Chloro-4-fluorophenyl)amino]-6-({4-[(R)-N-methyl-N-(tetrahydrofuran-2-ylmethyl)amino]-1-oxo-2-buten-1-yl}-amino)-7-cyclobutyloxyquinazoline

(56) 4-[(3-Chloro-4-fluorophenyl)amino]-6-({4-[(S)-N-methyl-N-(tetrahydrofuran-2-ylmethyl)amino]-1-oxo-2-buten-1-yl}-amino)-7-cyclobutyloxyquinazoline

(57) 4-[(3-Chloro-4-fluorophenyl)amino]-6-{[4-(pyrrolidin-1-yl)-1-oxo-2-buten-1-yl]amino}-7-cyclobutyloxyquinazoline

(58) 4-[(3-Chloro-4-fluorophenyl)amino]-6-{[4-(2-methylpyrrolidin-1-yl)-1-oxo-2-buten-1-yl]amino}-7-cyclobutyloxyquinazoline

(59) 4-[(3-Chloro-4-fluorophenyl)amino]-6-{[4-(2,5-dimethylpyrrolidin-1-yl)-1-oxo-2-buten-1-yl]amino}-7-cyclobutyloxyquinazoline

(60) 4-[(3-Chloro-4-fluorophenyl)amino]-6-{[4-(piperidin-1-yl)-1-oxo-2-buten-1-yl]amino}-7-cyclobutyloxyquinazoline

(61) 4-[(3-Chloro-4-fluorophenyl)amino]-6-{[4-(2-methylpiperidin-1-yl)-1-oxo-2-buten-1-yl]amino}-7-cyclobutyloxyquinazoline

(62) 4-[(3-Chloro-4-fluorophenyl)amino]-6-{[4-(2,6-dimethylpiperidin-1-yl)-1-oxo-2-buten-1-yl]amino}-7-cyclobutyloxyquinazoline

(63) 4-[(3-Chloro-4-fluorophenyl)amino]-6-{[4-(4-hydroxy-piperidin-1-yl)-1-oxo-2-buten-1-yl]amino}-7-cyclobutyloxyquinazoline

(64) 4-[(3-Chloro-4-fluorophenyl)amino]-6-{[4-(4-methoxy-piperidin-1-yl)-1-oxo-2-buten-1-yl]amino}-7-cyclobutyloxyquinazoline

(65) 4-[(3-Chloro-4-fluorophenyl)amino]-6-({4-[4-(2-methoxyethyl)piperazin-1-yl]-1-oxo-2-buten-1-yl}amino)-7-cyclobutyloxyquinazoline

(66) 4-[(3-Chloro-4-fluorophenyl)amino]-6-{[4-(3-methylmorphoin-4-yl)-1-oxo-2-buten-1-yl]amino}-7-cyclobutyloxyquinazoline

(67) 4-[(3-Chloro-4-fluorophenyl)amino]-6-{[4-(3,5-dimethyl-morpholin-4-yl)-1-oxo-2-buten-1-yl]amino}-7-cyclobutyloxyquinazoline

(68) 4-[(3-Chloro-4-fluorophenyl)amino]-6-({4-[N-methyl-N-(2-methoxyethyl)amino]-1-oxo-2-buten-1-yl}amino)-7-(tetrahydrofuran-3-yloxy)quinazoline

(69) 4-[(3-Chloro-4-fluorophenyl)amino]-6-({4-[N-methyl-N-(2-methoxyethyl)amino]-1-oxo-2-buten-1-yl}amino)-7-(tetrahydropyran-4-yloxy)quinazoline

(70) 4-[(3-Chloro-4-fluorophenyl)amino]-6-({4-[N-methyl-N-(2-methoxyethyl)amino]-1-oxo-2-buten-1-yl}amino)-7-(tetrahydrofuran-2-ylmethoxy)quinazoline

(71) 4-[(3-Chloro-4-fluorophenyl)amino]-7-[3-(azetidin-1-yl)propyloxy]-6-[(vinylcarbonyl)amino]quinazoline

(72) 4-[(3-Chloro-4-fluorophenyl)amino]-7-[3-(4-methylhomopiperazin-1-yl)propyloxy]-6-[(vinylcarbonyl)amino]quinazoline.

EXAMPLE 4

| Coated tablets containing 75 mg of active substance 1 tablet core contains: | |
| --- | --- |
| active substance | 75.0 mg |
| calcium phosphate | 93.0 mg |
| corn starch | 35.5 mg |
| polyvinylpyrrolidone | 10.0 mg |
| hydroxypropylmethylcellulose | 15.0 mg |
| magnesium stearate | 1.5 mg |
| | 230.0 mg |

Preparation:

The active substance is mixed with calcium phosphate, corn starch, polyvinylpyrrolidone, hydroxypropylmethylcellulose and half the specified amount of magnesium stearate. Blanks 13 mm in diameter are produced in a tablet-making machine and these are then rubbed through a screen with a mesh size of 1.5 mm using a suitable machine and mixed with the rest of the magnesium stearate. This granulate is compressed in a tablet-making machine to form tablets of the desired shape. Weight of core: 230 mg; die: 9 mm, convex. The tablet cores thus produced are coated with a film consisting essentially of hydroxypropylmethylcellulose. The finished film-coated tablets are polished with beeswax. Weight of coated tablet: 245 mg.

EXAMPLE 5

Tablets containing 100 mg of active substance
Composition:
1 tablet contains:

| | |
|---|---|
| active substance | 100.0 mg |
| lactose | 80.0 mg |
| corn starch | 34.0 mg |
| polyvinylpyrrolidone | 4.0 mg |
| magnesium stearate | 2.0 mg |
| | 220.0 mg |

Method of Preparation:

The active substance, lactose and starch are mixed together and uniformly moistened with an aqueous solution of the polyvinylpyrrolidone. After the moist composition has been screened (2.0 mm mesh size) and dried in a rack-type drier at 50° C. it is screened again (1.5 mm mesh size) and the lubricant is added. The finished mixture is compressed to form tablets. Weight of tablet: 220 mg; diameter: 10 mm, biplanar, facetted on both sides and notched on one side.

EXAMPLE 6

Tablets containing 150 mg of active substance
Composition:
1 tablet contains:

| | |
|---|---|
| active substance | 50.0 mg |
| powdered lactose | 89.0 mg |
| corn starch | 40.0 mg |
| colloidal silica | 10.0 mg |
| polyvinylpyrrolidone | 10.0 mg |
| magnesium stearate | 1.0 mg |
| | 300.0 mg |

Preparation:

The active substance mixed with lactose, corn starch and silica is moistened with a 20% aqueous polyvinylpyrrolidone solution and passed through a screen with a mesh size of 1.5 mm. The granules, dried at 45° C., are passed through the same screen again and mixed with the specified amount of magnesium stearate. Tablets are pressed from the mixture. Weight of tablet: 300 mg; die: 10 mm, flat.

EXAMPLE 7

Hard gelatine capsules containing 150 mg of active substance
1 capsule contains:

| | |
|---|---|
| active substance | 50.0 mg |
| corn starch (dried) | approx. 80.0 mg |
| lactose (powdered) | approx. 87.0 mg |
| magnesium stearate | 3.0 mg |
| | approx. 420.0 mg |

Preparation:

The active substance is mixed with the excipients, passed through a screen with a mesh size of 0.75 mm and homogeneously mixed using a suitable apparatus. The finished mixture is packed into size 1 hard gelatine capsules. Capsule filling: approx. 320 mg; capsule shell: size 1 hard gelatine capsule.

EXAMPLE 8

Suppositories containing 150 mg of active substance
1 suppository contains:

| | |
|---|---|
| active substance | 150.0 mg |
| polyethyleneglycol 1500 | 550.0 mg |
| polyethyleneglycol 6000 | 460.0 mg |
| polyoxyethylene sorbitan monostearate | 840.0 mg |
| | 2,000.0 mg |

Preparation:

After the suppository mass has been melted the active substance is homogeneously distributed therein and the melt is poured into chilled molds.

EXAMPLE 9

Suspension containing 50 mg of active substance
100 ml of suspension contain:

| | |
|---|---|
| active substance | 1.00 g |
| carboxymethylcellulose-Na-salt | 0.10 g |
| methyl p-hydroxybenzoate | 0.05 g |
| propyl p-hydroxybenzoate | 0.01 g |
| glucose | 10.00 g |
| glycerol | 5.00 g |
| 70% sorbitol solution | 20.00 g |
| flavoring | 0.30 g |
| dist. water | ad 100 ml |

Preparation:

The distilled water is heated to 70° C. The methyl and propyl p-hydroxybenzoates together with the glycerol and sodium salt of carboxymethylcellulose are dissolved therein with stirring. The solution is cooled to ambient temperature and the active substance is added and homogeneously dispersed therein with stirring. After the sugar, the sorbitol solution and the flavoring have been added and dissolved, the suspension is evacuated with stirring to eliminate air. 5 ml of suspension contain 50 mg of active substance.

EXAMPLE 10

Ampoules containing 10 mg active substance
Composition:

| | |
|---|---|
| active substance | 10.0 mg |
| 0.01 N hydrochloric acid | q.s. |
| double-distilled water | ad 2.0 ml |

Preparation:

The active substance is dissolved in the necessary amount of 0.01 N HCl, made isotonic with common salt, filtered sterile and transferred into 2 ml ampoules.

EXAMPLE 11

| Ampoules containing 50 mg of active substance Composition: | |
|---|---|
| active substance | 50.0 mg |
| 0.01 N hydrochloric acid | q.s. |
| double-distilled water | ad 10.0 ml |

Preparation:

The active substance is dissolved in the necessary amount of 0.01 N HCl, made isotonic with common salt, filtered sterile and transferred into 10 ml ampoules.

EXAMPLE 12

| Capsules for powder inhalation containing 5 mg of active substance 1 capsule contains: | |
|---|---|
| active substance | 5.0 mg |
| lactose for inhalation | 15.0 mg |
| | 20.0 mg |

Preparation:

The active substance is mixed with lactose for inhalation. The mixture is packed into capsules in a capsule-making machine (weight of the empty capsule approx. 50 mg). Weight of capsule: 70.0 mg; size of capsule=3.

EXAMPLE 13

| Solution for inhalation for hand-held nebulizers containing 2.5 mg active substance 1 spray contains: | |
|---|---|
| active substance | 2.500 mg |
| benzalkonium chloride | 0.001 mg |
| 1N hydrochloric acid | q.s. |
| ethanol/water (50/50) | ad 15.000 mg |

Preparation:

The active substance and benzalkonium chloride are dissolved in ethanol/water (50/50). The pH of the solution is adjusted with 1N hydrochloric acid. The resulting solution is filtered and transferred into suitable containers for use in hand-held nebulizers (cartridges). Contents of the container: 4.5 g.

What is claimed is:

1. A quinazoline compound of formula

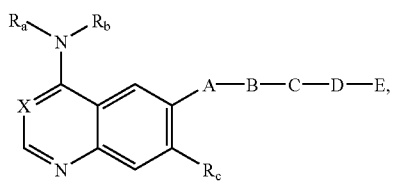

(I)

wherein $R_a$ denotes a hydrogen atom or a $C_{1-4}$-alkyl group, $R_b$ denotes a phenyl, benzyl or 1-phenylethyl group wherein the phenyl nucleus is substituted in each case by the groups $R_1$ to $R_3$, whilst $R_1$ and $R_2$, which may be identical or different, in each case denote a hydrogen, fluorine, chlorine, bromine or iodine atom, a $C_{1-4}$-alkyl, hydroxy, $C_{1-4}$-alkoxy, $C_{3-6}$-cycloalkyl, $C_{4-6}$-cycloalkoxy, $C_{2-5}$-alkenyl or $C_{2-5}$-alkynyl group, an aryl, aryloxy, arylmethyl or arylmethoxy group, a $C_{3-5}$-alkenyloxy or $C_{3-5}$-alkynyloxy group, whilst the unsaturated moiety may not be linked to the oxygen atom, a $C_{1-4}$-alkylsulfenyl, $C_{1-4}$-alkylsulfinyl, $C_{1-4}$-alkylsulfonyl, $C_{1-4}$-alkylsulfonyloxy, trifluoromethylsulfenyl, trifluoromethylsulfinyl or trifluoromethylsulfonyl group, a methyl or methoxy group substituted by 1 to 3 fluorine atoms, an ethyl or ethoxy group substituted by 1 to 5 fluorine atoms, a cyano or nitro group or an amino group optionally substituted by one or two $C_{1-4}$-alkyl groups, wherein the substituents may be identical or different, or $R_1$ together with $R_2$, if they are bound to adjacent carbon atoms, denote a —CH=CH—CH=CH group and $R_3$ denotes a hydrogen, fluorine, chlorine or bromine atom, a $C_{1-4}$-alkyl, trifluoromethyl or $C_{1-4}$-alkoxy group, X denotes a nitrogen atom, A denotes an imino group optionally substituted by a $C_{1-4}$-alkyl group, B denotes a carbonyl group, C denotes a —CH=C=CH—, >C=CH$_2$ or —CH=CH— group which may be substituted in each case by one or two methyl groups or by a trifluoromethyl group, an —C≡C— group or a —CH=CH—CH=CH— group optionally substituted by 1 to 4 methyl groups or by a trifluoromethyl group, D denotes an alkylene group wherein the alkylene moiety contains 1 to 8 carbon atoms and additionally 1 to 4 hydrogen atoms in the alkylene moiety may be replaced by fluorine atoms, E denotes an amino, $C_{1-4}$-alkylamino or di-($C_{1-4}$-alkyl)-amino group wherein the alkyl moieties may be identical or different, a $C_{2-4}$-alkylamino group wherein the alkyl moiety is substituted in β-, γ-, or δ-position with regard to the nitrogen atom of the amino group by the group $R_5$, whilst $R_5$ denotes a hydroxy, $C_{1-4}$-alkoxy, amino, $C_{1-4}$-alkylamino or di-($C_{1-4}$-alkyl)-amino group, an N-($C_{1-4}$-alkyl)-N-($C_{2-4}$-alkyl)-amino group wherein the $C_{2-4}$-alkyl moiety is substituted in β-, γ-, or δ-position with regard to the nitrogen atom of the amino group by the group $R_5$, whilst $R_5$ is as hereinbefore defined, a di-($C_{2-4}$-alkyl)-amino group wherein the two $C_{2-4}$-alkyl moieties are substituted in each case in β-, γ-, or δ-position with regard to the nitrogen atom of the amino group by the group $R_5$, whilst the substituents may be identical or different and $R_5$ is as hereinbefore defined, a $C_{3-7}$-cycloalkylamino or $C_{3-7}$-cycloalkyl-$C_{1-3}$-alkylamino group wherein in each case the nitrogen atom may be substituted by a further $C_{1-4}$-alkyl group, $R_c$ denotes a $C_{4-7}$-cycloalkoxy or $C_{3-7}$-cycloalkyl-$C_{1-6}$-alkoxy group wherein the cycloalkyl moiety in each case may be substituted by a $C_{1-3}$-alkyl, hydroxy, $C_{1-4}$-alkoxy, amino, $C_{1-4}$-alkylamino, di-($C_{1-4}$-alkyl)-amino, hydroxy-$C_{1-2}$-alkyl, $C_{1-4}$-alkoxy-$C_{1-2}$-alkyl, amino-$C_{1-2}$-alkyl, $C_{1-4}$-alkylamino-$C_{1-2}$-alkyl, or di-($C_{1-4}$-alkyl)-amino-$C_{1-2}$-alkyl group, whilst the abovementioned monosubstituted cycloalkyl moieties may additionally be substituted by a $C_{1-3}$-alkyl group, whilst by the aryl moieties mentioned in the definition of the abovementioned groups is meant a phenyl group which in each case may be monosubstituted by $R_7$, mono-, di- or trisubstituted by $R_8$ or monosubstituted by $R_7$ and additionally mono- or disubstituted by $R_8$, wherein the substituents may be identical or different and $R_7$ denotes a cyano, carboxy, $C_{1-4}$-alkoxycarbonyl, aminocarbonyl, $C_{1-4}$-alkylaminocarbonyl, di-($C_{1-4}$-alkyl)-aminocarbonyl, $C_{1-4}$-alkylsulfenyl, $C_{1-4}$-alkylsulfinyl, $C_{1-4}$-alkylsulfonyl, hydroxy, $C_{1-4}$-alkylsulfonyloxy, trifluoromethyloxy, nitro, amino, $C_{1-4}$-alkylamino, di-($C_{1-4}$-alkyl)-amino, $C_{1-4}$-alkylcarbonylamino, N-($C_{1-4}$-alkyl)-$C_{1-4}$-alkylcarbonylamino, $C_{1-4}$-alkylsulfonylamino, N-($C_{1-4}$-alkyl)-$C_{1-4}$-alkylsulfonylamino, aminosulfonyl, $C_{1-4}$-alkylaminosulfonyl or di-($C_{1-4}$-alkyl)-aminosulfonyl group, and $R_8$ denotes a fluorine, chlorine, bromine or iodine atom, a $C_{1-4}$-alkyl, trifluoromethyl or $C_{1-4}$-alkoxy group or two groups $R_8$, if they are bound to adjacent carbon atoms, together denote a $C_{3-5}$-alkylene or 1,3-butadien-1,4-ylene group, or the tautomers, or stereoisomers or pharmaceutically acceptable salts thereof.

2. The quinazoline of formula I according to claim 1, wherein $R_a$ denotes a hydrogen atom, $R_b$ denotes a phenyl, benzyl or 1-phenylethyl group wherein the phenyl nucleus is substituted in each case by the groups $R_1$ to $R_3$, whilst $R_1$ and $R_2$, which may be identical or different, in each case denote a hydrogen, fluorine, chlorine, bromine or iodine atom, a $C_{1-4}$-alkyl, hydroxy, $C_{1-4}$-alkoxy, $C_{3-6}$-cycloalkyl, $C_{4-6}$-cycloalkoxy, $C_{2-5}$-alkenyl or $C_{2-5}$-alkynyl group, an aryl, aryloxy, arylmethyl or arylmethoxy group, a methyl or methoxy group substituted by 1 to 3 fluorine atoms, a cyano or nitro group and $R_3$ denotes a hydrogen, fluorine, chlorine or bromine atom, a $C_1$-alkyl, trifluoromethyl or $C_{1-4}$-alkoxy group, X denotes a nitrogen atom, A denotes an imino group, B denotes a carbonyl group, C denotes a —CH=C=CH—, >C=CH$_2$ or —CH=CH— group, an —C≡C— or —CH=CH—CH=CH— group, D denotes an alkylene group wherein the alkylene moiety in each case contains 1 to 4 carbon atoms and additionally 1 to 4 hydrogen atoms in the alkylene moiety may be replaced by fluorine atoms, E denotes a di-($C_{1-4}$-alkyl)-amino group wherein the alkyl moieties may be identical or different, an N-($C_{1-4}$-alkyl)-N-($C_{2-4}$-alkyl)-amino group wherein the $C_{2-4}$-alkyl moiety is substituted in β-, γ-, or δ-position with regard to the nitrogen atom of the amino group by the group $R_5$, where $R_5$ denotes a hydroxy, $C_{1-4}$-alkoxy or di-($C_{1-4}$-alkyl)-amino group, a di-($C_{2-4}$-alkyl)-amino group wherein the two $C_{2-4}$-alkyl moieties in each case are substituted in β-, γ-, or δ-position with regard to the nitrogen atom of the amino group by the group $R_5$, wherein the substituents may be identical or different and $R_5$ is as hereinbefore defined, a $C_{3-7}$-cycloalkylamino or $C_{3-7}$-cycloalkyl-$C_{1-3}$-alkylamino group wherein in each case the nitrogen atom is substituted by a further $C_{1-4}$-alkyl group, $R_c$ denotes a $C_{4-7}$-cycloalkoxy or $C_{3-7}$-cycloalkyl-$C_{1-6}$-alkoxy group wherein the cycloalkyl moiety in each case may be substituted by a $C_{1-3}$-alkyl, hydroxy, $C_{1-4}$-alkoxy, di-($C_{1-4}$-alkyl)-amino, hydroxy-$C_{1-2}$-alkyl, $C_{1-4}$-alkoxy-$C_{1-2}$-alkyl, or di-($C_{1-4}$-alkyl)-amino-$C_{1-2}$-alkyl group, whilst the abovementioned monosubstituted cycloalkyl moieties may additionally be substituted by a $C_{1-3}$-alkyl group, whilst by the aryl moieties mentioned in the definition of the abovementioned groups is meant a phenyl group which may in each case be monosubstituted by $R_7$, mono-, di- or trisubstituted by $R_8$ or monosubstituted by $R_7$ and additionally mono- or disubstituted by $R_8$, wherein the substituents may be identical or different and $R_7$ denotes a cyano, carboxy, $C_{1-4}$-alkoxycarbonyl, aminocarbonyl, $C_{1-4}$-alkylaminocarbonyl, di-($C_{1-4}$-alkyl)-aminocarbonyl, $C_{1-4}$-alkylsulfenyl, $C_{1-4}$-alkylsulfinyl, $C_{1-4}$-alkylsulfonyl, hydroxy, $C_{1-4}$-alkylsulfonyloxy, trifluoromethyloxy, nitro, amino, $C_{1-4}$-alkylamino, di-($C_{1-4}$-alkyl)-amino, $C_{1-4}$-alkylcarbonylamino, N-($C_{1-4}$-alkyl)-$C_{1-4}$-alkylcarbonylamino, $C_{1-4}$-alkylsulfonylamino, N-($C_{1-4}$-alkyl)-$C_{1-4}$-alkylsulfonylamino, aminosulfonyl, $C_{1-4}$-alkylaminosulfonyl or di-($C_{1-4}$-alkyl)-aminosulfonyl group, and $R_8$ denotes a fluorine, chlorine, bromine or iodine atom, a $C_{1-4}$-alkyl, trifluoromethyl or $C_{1-4}$-alkoxy group or two groups $R_8$, if they are bound to adjacent carbon atoms, together denote a $C_{3-5}$-alkylene or 1,3-butadien-1,4-ylene group, or the tautomers, or stereoisomers or pharmaceutically acceptable salts thereof.

3. The quinazoline of formula I according to claim 1, wherein $R_a$ denotes a hydrogen atom, $R_b$ denotes a phenyl, benzyl or 1-phenylethyl group wherein the phenyl nucleus is substituted in each case by the groups $R_1$ and $R_2$, where $R_1$ and $R_2$, which may be identical or different, in each case denote a hydrogen, fluorine, chlorine or bromine atom, a methyl, trifluoromethyl or methoxy group, X denotes a nitrogen atom, A denotes an imino group, B denotes a carbonyl group, C denotes a —CH=CH— group, an —C≡C— or —CH=CH—CH=CH— group, D denotes a $C_{1-4}$-alkylene group, E denotes a di-($C_{1-4}$-alkyl)-amino group wherein the alkyl moieties may be identical or different, an N-($C_{1-4}$-alkyl)-N-($C_{2-4}$-alkyl)-amino group wherein the $C_{2-4}$-alkyl moiety is substituted in β-, γ-, or δ-position with regard to the nitrogen atom of the amino group by the group $R_5$, whilst
$R_5$ denotes a hydroxy, $C_{1-3}$-alkoxy or di-($C_{1-3}$-alkyl)-amino group,
a di-($C_{2-4}$-alkyl)-amino group wherein the two $C_{2-4}$-alkyl moieties in each case are substituted in β-, γ-, or δ-position with regard to the nitrogen atom of the amino group by the group $R_5$, wherein the substituents may be identical or different and $R_5$ is as hereinbefore defined,
a $C_{3-5}$-cycloalkylamino or $C_{3-5}$-cycloalkyl-$C_{1-3}$-alkylamino group wherein in each case the nitrogen atom is substituted by a further $C_{1-3}$-alkyl group,
$R_c$ denotes a $C_{4-7}$-cycloalkoxy or $C_{3-7}$-cycloalkyl-$C_{1-4}$-alkoxy group wherein the cycloalkyl moiety in each case may be substituted by a $C_{1-3}$-alkyl or $C_{1-3}$-alkoxy group, or the tautomers, or stereoisomers or pharmaceutically acceptable salts thereof.

4. The quinazoline of formula I according to claim 1, wherein
$R_a$ denotes a hydrogen atom,
$R_b$ denotes a phenyl, benzyl or 1-phenylethyl group, whilst the phenyl nucleus is substituted in each case by the radicals $R_1$ and $R_2$, whilst
$R_1$ and $R_2$, which may be identical or different, each denotes a hydrogen, fluorine, chlorine or bromine atom,
X denotes a nitrogen atom,
A denotes an imino group,
B denotes a carbonyl group,
C denotes a —CH═CH—, —C≡C— or —CH═CH—CH═CH— group,
D denotes an $C_{1-3}$-alkylene group,
E denotes a di-($C_{1-4}$-alkyl)-amino group, wherein the alkyl moieties may be identical or different,
a methylamino or ethylamino group each substituted at the nitrogen atom by a 2-methoxy-ethyl, 1-methoxy-2-propyl, 2-methoxypropyl, 3-methoxypropyl, cyclopropyl or cyclopropylmethyl group,
a bis-(2-methoxyethyl)amino group,
$R_c$ denotes a cyclopropylmethoxy, cyclobutylmethoxy, cyclopentylmethoxy or cyclohexylmethoxy group,
a cyclobutyloxy, cyclopentyloxy or cyclohexyloxy group, or the tautomers, or stereoisomers or pharmaceutically acceptable salts thereof.

5. The quinazoline of formula I according to claim 1, wherein
$R_a$ denotes a hydrogen atom,
$R_b$ denotes a 1-phenylethyl group or a phenyl group wherein the phenyl nucleus is substituted by the radicals $R_1$ and $R_2$, whilst
$R_1$ and $R_2$, which may be identical or different, each denote a hydrogen, fluorine, chlorine or bromine atom,
X denotes a nitrogen atom,
A denotes an imino group,
B denotes a carbonyl group,
C denotes a —CH═CH—, —C≡C— or —CH═CH—CH═CH— group,
D denotes a methylene group,
E denotes a dimethylamino, diethylamino, Bis(2-methoxyethyl)amino, N-methyl-N-(2-methoxyethyl)amino, N-ethyl-N-(2-methoxyethyl)amino, N-methyl-N-cyclopropylamino,
N-methyl-N-cyclopropylmethyl-amino, N-methyl-N-(1-methoxy-2-propyl)amino, N-methyl-N-(2-methoxypropyl)amino or N-methyl-N-(3-methoxypropyl)amino group,
$R_c$ denotes a cyclopropylmethoxy, cyclobutyloxy or cyclopentyloxy group,
or the tautomers, or stereoisomers or pharmaceutically acceptable salts thereof.

6. The following compound of general formula I according to claim 1:
4-[(3-Chloro-4-fluorophenyl)amino]-6-{[4-(N,N-diethylamino)-1-oxo-2-buten-1-yl]amino}-7-cyclopropylmethoxyquinazoline
or a pharmaceutically acceptable salt thereof.

7. The physiologically acceptable salt of a compound according to one of claims 1 to 6 with an inorganic or organic acid or base.

8. A pharmaceutical composition comprising a compound according to claim 7, together with an inert carrier and with or without a diluent.

9. A method for treating a disease comprising administering a pharmaceutical composition according to claim 8, wherein said disease is selected from the group consisting of: malignant tumors, diseases of the airways and lungs and diseases of the gastrointestinal tract and the bile duct and gall bladder.

* * * * *

UNITED STATES PATENT AND TRADEMARK OFFICE
CERTIFICATE OF CORRECTION

PATENT NO. : 7,220,750 B2 Page 1 of 1
APPLICATION NO. : 10/016280
DATED : May 22, 2007
INVENTOR(S) : Frank Himmelsbach et al.

It is certified that error appears in the above-identified patent and that said Letters Patent is hereby corrected as shown below:

Title Page, under the heading Related U.S. Application Data, please correct the entry to read:

(63)
Continuation of Application No PCT/EP00/05547, filed June 16, 2000, which claimed the benefit of Provisional Application No. 60/146,644, filed July 30, 1999, and German Application Nos. DE 199280281.1 and DE 10023085.7, filed June 21, 1999 and Mary 11, 2000, respectively.

Signed and Sealed this

Seventeenth Day of July, 2007

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,220,750 B2 | Page 1 of 1 |
| APPLICATION NO. | : 10/016280 | |
| DATED | : May 22, 2007 | |
| INVENTOR(S) | : Frank Himmelsbach et al. | |

It is certified that error appears in the above-identified patent and that said Letters Patent is hereby corrected as shown below:

Title Page, under the heading Related U.S. Application Data, please correct the entry to read:

(63)
Continuation of Application No PCT/EP00/05547, filed June 16, 2000, which claimed the benefit of Provisional Application No. 60/146,644, filed July 30, 1999, and German Application Nos. DE 199280281.1 and DE 10023085.7, filed June 21, 1999 and May 11, 2000, respectively.

This certificate supersedes Certificate of Correction issued July 17, 2007.

Signed and Sealed this

Twenty-first Day of August, 2007

JON W. DUDAS
*Director of the United States Patent and Trademark Office*